United States Patent
Ishizuki et al.

(10) Patent No.: US 10,578,557 B2
(45) Date of Patent: Mar. 3, 2020

(54) GRAIN QUALITY LEVEL DISCRIMINATION DEVICE

(71) Applicant: SATAKE CORPORATION, Chiyoda-ku, Tokyo (JP)

(72) Inventors: Hiroki Ishizuki, Tokyo (JP); Akira Eto, Tokyo (JP); Takahiro Doi, Tokyo (JP); Hiroaki Takeuchi, Tokyo (JP)

(73) Assignee: SATAKE CORPORATION, Tokyo (JP)

( * ) Notice: Subject to any disclaimer, the term of this patent is extended or adjusted under 35 U.S.C. 154(b) by 0 days.

(21) Appl. No.: 15/536,723

(22) PCT Filed: Dec. 18, 2015

(86) PCT No.: PCT/JP2015/085494
§ 371 (c)(1),
(2) Date: Jun. 16, 2017

(87) PCT Pub. No.: WO2016/098882
PCT Pub. Date: Jun. 23, 2016

(65) Prior Publication Data
US 2017/0350825 A1    Dec. 7, 2017

(30) Foreign Application Priority Data

Dec. 19, 2014 (JP) ................. 2014-257928
Dec. 26, 2014 (JP) ................. 2014-265410
Dec. 26, 2014 (JP) ................. 2014-266583

(51) Int. Cl.
*G01N 21/85* (2006.01)
*A01D 41/127* (2006.01)
(Continued)

(52) U.S. Cl.
CPC .......... *G01N 21/85* (2013.01); *A01D 41/1277* (2013.01); *G01N 21/55* (2013.01);
(Continued)

(58) Field of Classification Search
CPC ............ G01N 21/85; G01N 21/8806; G01N 21/8851; G01N 21/55; G01N 2201/062;
(Continued)

(56) References Cited

U.S. PATENT DOCUMENTS

| 6,013,887 A | 1/2000 | Satake et al. |
| 2006/0153738 A1 | 7/2006 | Tanji |

(Continued)

FOREIGN PATENT DOCUMENTS

| JP | S61-191944 A | 8/1986 |
| JP | H05-90353 U | 12/1993 |

(Continued)

OTHER PUBLICATIONS

Machine translation for JP2002-202265 (Year: 2002).*

*Primary Examiner* — Qian Yang
(74) *Attorney, Agent, or Firm* — Drinker Biddle & Reath LLP

(57) ABSTRACT

An object of the present invention is to improve the quality level discrimination accuracy of the grain G by a grain quality level discrimination device. The device includes an optical unit 3 that emits light to the grain G, receives reflected and/or transmitted light from the grain G by a photosensor, and obtains information for discrimination of the quality level of the grain G from the upper and lower surface side of the grain G, and a quality level discrimination unit 7 that discriminates the quality level of the grain G on the basis of the information. The information on the upper and lower surface sides can be acquired by one optical unit at the same time so that the divergence therebetween due to the displacement or variation of the attitude of the grain G can be avoided. The reference plate for the correction of the information is placed outside of the moving path of the grain G to prevent it from soiling or damaging. Thus the deterioration of information can be avoided. Further, a reference plate especially for the information to be obtained from the side surface of the grain G may be provided for enhancing the accuracy of the side surface information. Thus the (Continued)

quality level discrimination accuracy can be improved further.

6 Claims, 17 Drawing Sheets

(51) Int. Cl.
    *G01N 21/55*          (2014.01)
    *G01N 21/88*          (2006.01)
    *G01N 21/27*          (2006.01)

(52) U.S. Cl.
    CPC ..... *G01N 21/8806* (2013.01); *G01N 21/8851* (2013.01); *G01N 21/274* (2013.01); *G01N 2021/8835* (2013.01); *G01N 2201/062* (2013.01)

(58) Field of Classification Search
    CPC ......... G01N 21/274; G01N 2021/8835; A01D 41/1277
    See application file for complete search history.

(56) References Cited

U.S. PATENT DOCUMENTS

| | | | |
|---|---|---|---|
| 2007/0127018 A1* | 6/2007 | Lindner | G01N 21/90 356/240.1 |
| 2013/0172735 A1* | 7/2013 | Andre | A61B 5/0066 600/425 |

FOREIGN PATENT DOCUMENTS

| | | | |
|---|---|---|---|
| JP | 2002-202265 | * | 7/2002 |
| JP | 2002-202265 A | | 7/2002 |
| JP | 2004-132706 A | | 4/2004 |
| JP | 2004-205463 A | | 7/2004 |
| JP | 2005-77221 A | | 3/2005 |
| JP | 2006-200945 A | | 8/2006 |
| JP | 2007-322206 A | | 12/2007 |
| JP | 2014-36969 A | | 2/2014 |
| JP | 2014-157086 A | | 8/2014 |

* cited by examiner (a)

(b)

(a)

(b)

GRAIN QUALITY LEVEL DISCRIMINATION DEVICE

CROSS REFERENCE TO PRIOR APPLICATIONS

This application is the National Stage of International Application No. PCT/JP2015/085494 filed Dec. 18, 2015 and claims benefit of Japanese Application No. 2014-257928 filed on Dec. 19, 2014; Japanese Application No. 2014-265410 filed on Dec. 26, 2014 and Japanese Application No. 2014-266583 filed on Dec. 26, 2014, which are herein incorporated by reference in their entirety.

TECHNICAL FIELD

The present invention relates to a grain quality level discrimination device for discriminating grain quality level.

BACKGROUND ART

A grain quality level discrimination device emitting light to grains, receiving a reflected and/or transmitted light from the grains, and discriminating the quality level of the grains on the basis of a received signal is well known in the art (for example, see Patent Literature 1).

The grain quality level discrimination device of the Patent Literature 1 includes a conveying unit for conveying grains, two optical detection units arranged in the conveying direction of the conveying unit, and a quality level discrimination unit.

The first optical detection unit of the grain quality level discrimination device is provided with a red light emitting diode lamp that emits red light obliquely from above to the grain, a green light emitting diode lamp that emits green light, and a blue light emitting diode lamp that emits blue light from below to the grain. The first optical detection unit is also provided with a RGB image sensor for receiving reflected or transmitted light from the upper and side surfaces of the grain illuminated by the lamps.

The second optical detection unit of the grain quality level discrimination device is also provided with a green light emitting diode lamp that emits green light obliquely from above to the grain, a blue light emitting diode lamp that emits blue light from above to the grain, and a red light emitting diode lamp that emits red light obliquely from below to the grain. The second optical detection unit is also provided with, a RGB image sensor that receives reflected or transmitted light emitted from the respective lamps from the lower surface of the grain.

The grain quality level discrimination device identifies the upper surface (planar) shape of the grain on the basis of the blue light transmitted through the grain and received by the RGB image sensor. The grain quality level discrimination device further acquires "upper-side information" of the grain such as color information, stain information, transparency information, and the like on the basis of the red, green, and blue lights from the upper surface of the grain received by the RGB image sensor.

Also, in the quality level discrimination unit, the shape of the side surface of the grain is identified on the basis of the transmitted light of any color from the side surface of the grain and received by the RGB image sensor of the first optical detection unit, so that "grain thickness information" of the grain is obtained on the basis of the shape of the side surface of the grain.

Further, the quality level discrimination unit identifies the lower surface (planar) shape of the grain on the basis of the transmitted blue light from the lower surface of the grain, the transmitted light being received by the RGB image sensor of the second optical detection unit, so as to obtain "lower-side information" of the grain such as stain information, crack information, and the like on the basis of the red, green, and blue lights from the lower surface of the grain that has been received by the RGB image sensor.

According to the grain quality level discrimination device described in Patent Literature 1, the quality of the grain conveyed by the conveying unit can be discriminated accurately by the "upper-side information" and the "grain thickness information" obtained on the basis of the reflected and/or transmitted light from the upper and side surfaces of the grain and received by the RGB image sensor of the first optical detection unit, and the "lower-side information" of the grain obtained on the basis of the reflected and/or transmitted light from the lower surface of the grain and received by the RGB image sensor of the second optical detection unit.

However, since the grain quality level discrimination device includes two identical optical detection units having the same scanning speed, the device involves the problem that it needs a large arrangement space and the size of the device becomes large, causing cost increases.

The grain quality level discrimination device includes a pair of the optical detection units disposed along the grain conveying direction, so that it is not possible to receive the reflected or transmitted light from the upper and side surfaces of the grain and that from the lower surface of the grain lower surface at the same time. As a result, if there is a small difference in the conveying speeds upon passing through the optical detection units, then the amount (number of times) of the light reception signal from the upper and lower surfaces of one grain can be differed (i.e. the problem of instability of the moving speed exists). Also, if the attitudes of the grain at the time of passing the two optical detection units are not completely identical with each other, then the identified planar shape differs between the upper and lower surfaces of the one grain (i.e. the problem of variation of the attitude of the grain in the course of the conveyance exists). Upon taking these problems into account, it is clear that there is room for improving the accuracy of discrimination of the quality level of the grain.

In order to solve the above mentioned problems, it might be better to receive the reflected and/or transmitted light from the upper, lower, and side surfaces of the grain simultaneously by one single optical detection unit of the grain quality level discrimination device. However, with regard to the side to be irradiated with the blue light required for identifying the planar shape of the grain, traditionally, the light source that emits the blue light interferes with the reception of the reflected and/or transmitted light from the grain.

Although the grain quality level determining devices disclosed in Patent Literatures 2 and 3 are of the same or similar structure as those of Patent Literature 1, a reference plate provided at any recess of a rotating disk is referred therein.

The grain quality level discriminating devices of Patent Literatures 2 and 3 is adapted to correct by using the reference plate, the variation of the characteristics of the optical elements such as the light sources and the photosensors of the optical detection unit due to the influence of the variation of the temperature inside of the main body and the like. However, the reference plate provided at the recess of the rotating disk of the grain conveying unit is apt to be scratched and stained by the grain and the like supplied thereto and brought into contact therewith, so that it leads to the degradation in the accuracy of the quality level discrimination of of the grains.

Also, in accordance with the above-described grain quality level discrimination device, the reference plate is provided at the recess of the rotating disk of the grain conveying unit, so that, when the reference plate is damaged, any broken piece of it may be mixed into the grains supplied onto the rotating disk.

Further, the grain quality level discrimination device described in Patent Literature 4 is well known. However, the grain quality level discrimination device described in Patent Literature 4 adopts a scheme of correction that uses reflected light from a reference plate of the rectangular parallelepiped shape mounted in a planar fashion to a recess in a rotating disk. In this connection, the amount of light received from the side surface of the reference plate is very small and it is not possible to obtain a correction coefficient with regard to the side surface side information. As a result, there is a problem that the correction had not been made successfully.

CITATION LIST

Patent Literature

[Patent Literature 1] Japanese Patent Laid-Open No. 2002-202265
[Patent Literature 2] Japanese Patent Laid-Open No. 2006-200945
[Patent Literature 3] Japanese Utility Model Laid-Open No. H5-90353
[Patent Literature 4] Japanese Patent Laid-Open No. 2006-200945

SUMMARY OF INVENTION

Technical Problem

A problem addressed by this invention is to improve the accuracy of discrimination of the quality level of the grain by the grain quality level discrimination device.

Solution to Problem

In order to achieve the above-identified objective, the grain quality level discrimination device of the present invention basically comprises an optical unit having a plurality of light sources that emit light to a grain and a photosensor that receives, from the grain, reflected and/or transmitted light emitted from the light source, and a quality level discrimination unit that discriminates the quality level of the grain on the basis of the light received by the photosensor.

In addition, the following features are adopted such that the reflected or transmitted light from the grain can also be received on the side where the particular light required for identifying the planar shape of the grain is to be emitted, and such that, at least the reflected and/or transmitted light from the upper and lower surfaces of the grain can simultaneously be received by one single optical unit.

The optical unit includes a particular light source configured to emit from one surface side of the grain a particular light having a predetermined wavelength required for identifying a planar shape of the grain, the photosensor includes a first light receiving area configured to receive reflected and/or transmitted light from the other surface side of the grain and a second light receiving area configured to receive reflected and/or transmitted light from one surface side of the grain, and an optical filter configured to transmit or reflect the particular light emitted by the particular light source is provided on the one surface side of the grain.

It should be noted that, the "one surface side" of the grain refers to the lower surface side of the grain placed on the conveying unit. Accordingly, the other surface side is the upper surface side of the grain.

In addition, the device is configured such that the particular light source is configured to emit the particular light from the one surface side of the grain through the optical filter, the first light receiving area is configured to receive the reflected and/or transmitted light from the other surface side of the grain including the transmitted light of the particular light from the particular light source emitted from the one surface side of the grain, and the second light receiving area is configured to receive the reflected and/or transmitted light from the one surface side of the grain through the optical filter.

Also, in accordance with the present invention, a reference plate can be provided for correcting the amount of light received by the photosensor. The amount of light received may affect the quality level discrimination of the grain. In this case, the following features are adopted to ensure that the scratches, stains, and the like due to contact with the grain or the like supplied onto the conveying unit are not produced on the reference plate, and thereby prevent degradation of the discrimination accuracy of the quality level discrimination unit due to the fluctuation of the amount of correction caused by the scratches, stains, and the like, and thus solve the problem. Further, as a result, these features define a structure that prevents broken pieces of the reference plate from being mixed into the grains supplied onto the conveying unit when the reference plate is damaged.

Specifically, the grain quality level discrimination device is configured such that it includes a conveying unit adapted to convey a grain, an optical unit having a light source adapted to emit light to the grain conveyed by the conveying unit and a photosensor adapted to receive reflected and/or transmitted light from the grain, a quality level discrimination unit configured to discriminate quality level of the grain on the basis of an amount of light received by the photosensor, and a reference plate for correction of the amount of light received by the photosensor.

In addition, the reference plate is provided and arranged at a position different from that of the conveying unit, and the optical unit is provided and arranged such that the optical unit is able to be shifted between a first position where the light source emits light to the grain and the photosensor receives the reflected and/or transmitted light from the grain and a second position where the light source emits light to the reference plate and the photosensor receives reflected and/or transmitted light from the reference plate.

Further, in accordance with the present invention, the grain quality level discrimination device may be configured such that a part of the reference plate is configured as a side-surface reference plate for correction of the amount of the reflected and/or transmitted light received from the side surface of the grain by the photosensor, and the side-surface reference plate has a reflection surface configured to reflect sideways the lights emitted from the upper and/or lower surface side light source.

Advantageous Effects of Invention

According to the grain quality level discrimination device of the present invention, the optical unit is provided with an optical filter on the one surface side of the grain for transmitting or reflecting the particular light emitted by the particular light source, the particular light source emits the particular light from the one surface side of the grain through the optical filter, the first light receiving area is configured to receive the reflected and/or transmitted light from the other surface side of the grain including the transmitted light of the particular light emitted from the particular light source on the one surface side of the grain, and the second light receiving area is configured to receive the reflected and/or transmitted light from the one surface side of the grain through the optical filter, so that on the other surface side of the grain, the first light receiving area receives the reflected and/or transmitted light from the other surface side of the grain including the transmitted light of the particular light from the particular light source required for identifying the planar shape of the grain, whilst, on the one surface side of the grain, the second light receiving unit receives the reflected or transmitted light from the one surface side of the grain G regardless of the presence of the particular light source on the one surface side of the grain.

In accordance with the present invention, the reflected and/or transmitted light from two surfaces, i.e. the upper and lower surfaces of one grain can be received at the same time by one single optical unit.

In this connection, although in the prior art, the reflected and/or transmitted lights are received independently by two optical units provided and arranged at positions away from each other in the conveying direction of the grains, in the present invention the lights are received at one single location, so that it is not affected by any instability in the conveying speed, and the reflected and/or transmitted light can be received at the same conveying speed. Thus it's possible to make the amount (number of times) of the light reception signals on the upper and lower surfaces of one grain identical with each other. Also, since the light can be received from the grain in the same attitude, it's possible to obtain the planar shape of the upper and lower surfaces of the grain as data obtained in the same attitude. Accordingly, the quality level discrimination accuracy of the grain can be enhanced.

The size of the device can be reduced by integrating multiple optical units into one single optical unit, and man-hours associated with attaching optical units in the device manufacturing process can also be reduced. In particular, since the process for attaching the optical unit requiring high accuracy, the manufacturing costs can also be reduced.

Further, according to the grain quality level discrimination device of the present invention, the reference plate is provided and arranged at a position different from that of the conveying unit, and the optical unit is provided and arranged so as to be able to be shifted between the first position where the light source emits light to the grain and the photosensor receives the reflected and/or transmitted light from the grain and the second position where the light source emits light to the reference plate and the photosensor receives reflected and/or transmitted light from the reference plate, so that scratches, stains, and the like are not created on the reference plate due to the contact with the grains or the like supplied onto the conveying unit, and disturbances on the correction of the amount of light received from the photosensor due to the scratches, stains, and the like on the reference plate are not caused. As a result, the discrimination accuracy of the the quality level discrimination unit is increased.

In the grain quality level discrimination device of the present invention, scratches, stains, and the like are not created on the reference plate due to the contact with the grains or the like supplied onto the conveying unit, so that the replacement frequency of the reference plate is remarkably decreased when compared with conventional ones, and the operations associated with the replacement of the reference plate and the burden of the operations associated with setting the reference quantity of light in response to the replacement of the reference plate are remarkably reduced.

Further, according to the grain quality level discrimination device of the present invention, since the replacement frequency of the reference plate is remarkably decreased, the device is less susceptible to the differences of the individual reference plates, and the accuracy of the discrimination of the quality level of the grain becomes stable.

It should be noted that, in the context of the above-described grain quality level discrimination device, when scratches, stains, and the like are created on the reference plate or when the reference plate is damaged, replacement of the reference plate may be taken into consideration. However, reference plates have individual differences and the reference quantity of light differ from one reference plate to another, so that it is necessary to perform the setting operations and the like again associated with the reference quantity of light from scratch every time the reference plate is to be replaced, which after all will not contribute to stability of the accuracy of the quality level discrimination of the grain.

Further, according to the grain quality level discrimination device of the present invention, the reference plate is a side-surface reference plate for correction of the amount of the reflected and/or transmitted light received from the side surface of the grain by the photosensor, and the side-surface reference plate has the reflection surface configured to reflect sideways the lights emitted from the upper and/or lower surface side light sources, so that the side surface side photosensor receives the reflected and/or transmitted light from the side surface of the side-surface reference plate of the amount substantially the same level as that of the light received from the side surface of the grain.

Accordingly, it's possible to calculate the amount of correction with a sufficient amount of light received and to correct the amount of the reflected and/or transmitted light received from the side surface of the grain. The amount of light received is used in recognition of the shape of the side surface of the grain to be measured, for example, by a binarization process. When binarization is carried out, the amount of light received does not frequently exhibit a deviation from the true value, and situations do not occur where the shape of the side surface of the grain is recognized to be larger or smaller than its actual size. Specifically, it's possible to correctly recognize the shape of the side surface of the grain by virtue of the corrected amount of light received and to increase the accuracy of the quality level discrimination of the grain.

DESCRIPTION OF EMBODIMENTS

Embodiments of the present invention will now be described with reference to the drawings.

Embodiment 1-1

Figure 1:
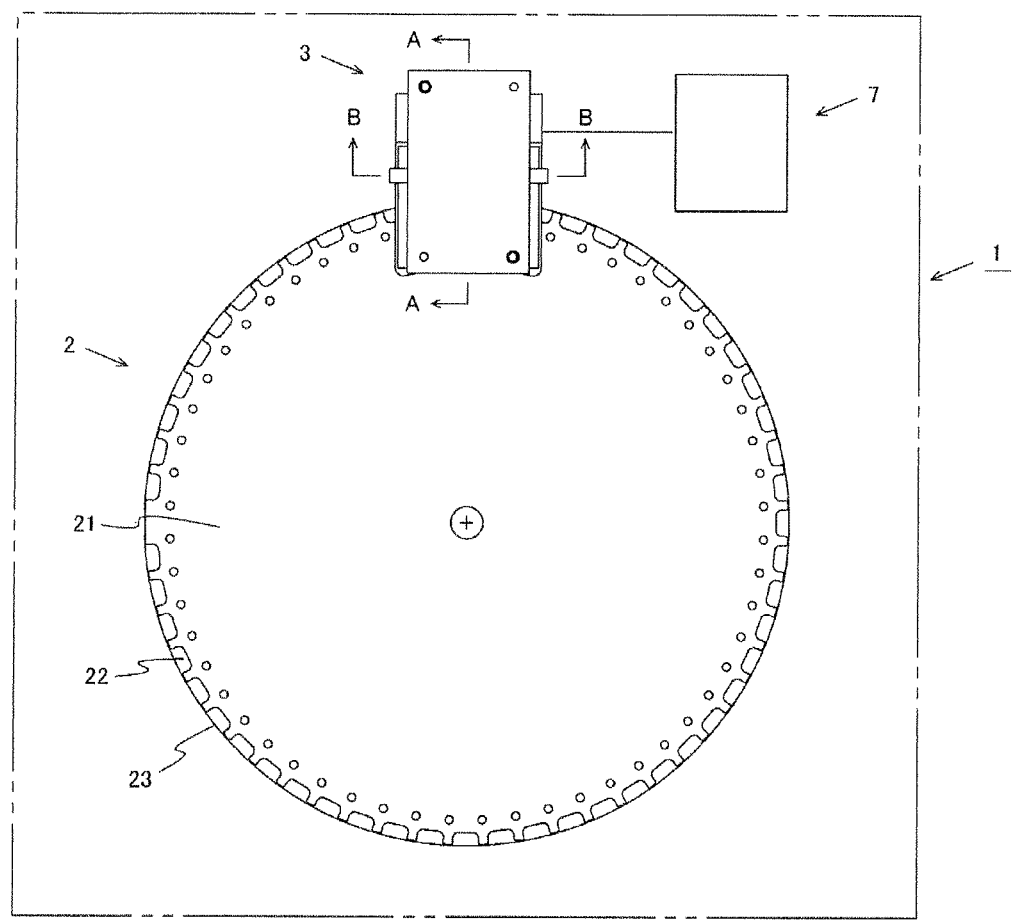
FIG. 1 is a schematic explanatory diagram of a grain quality level discrimination device in accordance with an embodiment 1-1 of the present invention illustrating a conveying unit, an optical unit, and a quality level discrimination unit in a schematic plan view.

FIG. 1 is a schematic explanatory diagram of a grain quality level discrimination device in accordance with an embodiment 1-1 of the present invention.

The grain quality level discrimination device 1 includes a conveying unit 2 for conveying a grain G, an optical unit 3 that emits light to the grain G and receives reflected and/or transmitted light from the grain G, and a quality level discrimination unit 7 that discriminates quality level of the grain G.

The conveying unit 2 has a disk 21 rotationally driven by a driving motor not-shown. Numerous recesses 22 are formed in the peripheral edge of the disk 21 and a transparent bottom plate 23 is provided in each recess 22.

The optical unit 3 has light sources for emitting light to the grain G and sensors for receiving from the grain G reflected and/or transmitted light originated from the emitted light. The optical unit 3 is arranged radially at a portion of the disk 21 of the conveying unit 2.

The optical unit 3 emits light to the grains G contained in each recess 22 of the disk 21 from the light source. The grains G are supplied onto the disk 21 and continuously conveyed in the course of the rotation of the disk 21. The reflected and/or transmitted light are received by the photosensors to provide light reception signals.

The quality level discrimination unit 7 is configured to discriminate the quality level of the grain G on the basis of the signals obtained by the optical unit 3. With regard to the quality level discrimination unit 7, for example, the arrangement as illustrated in Japanese Patent Laid-Open No. 2002-202265 and other various arrangements can be adopted.

Figure 2:
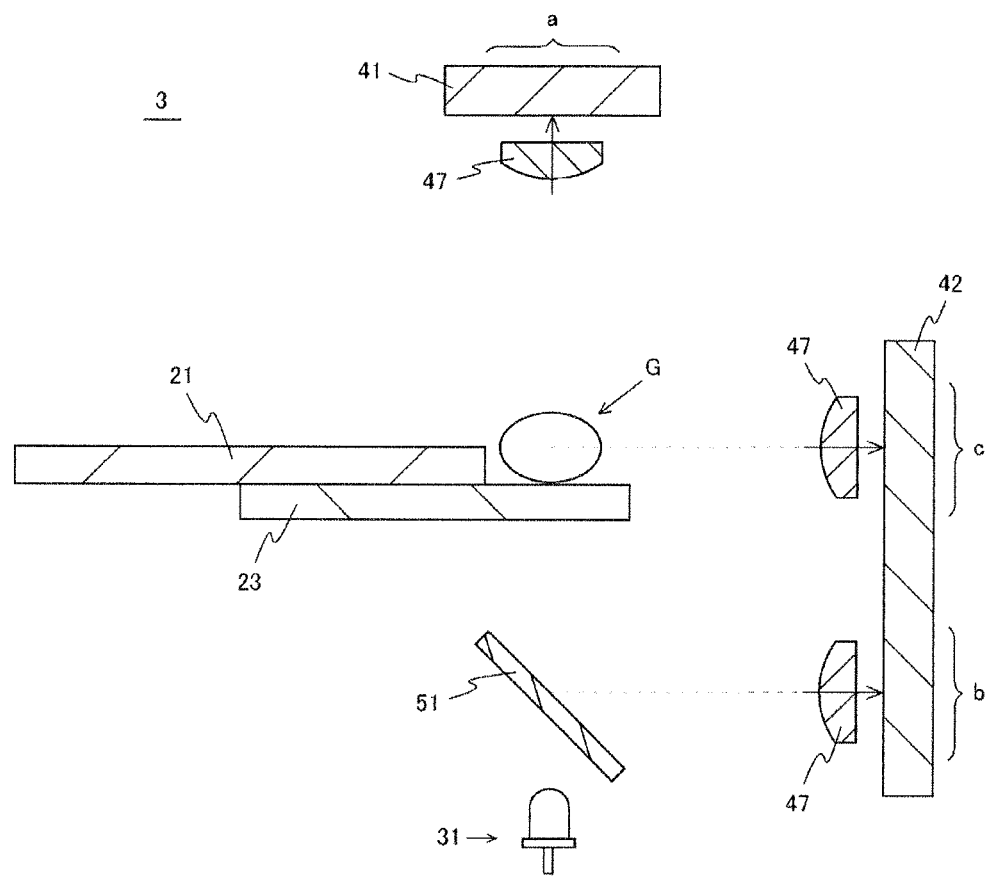
FIG. 2 is an explanatory diagram of the optical unit illustrating a schematic diagram of the A-A cross section of FIG. 1.
Figure 3:
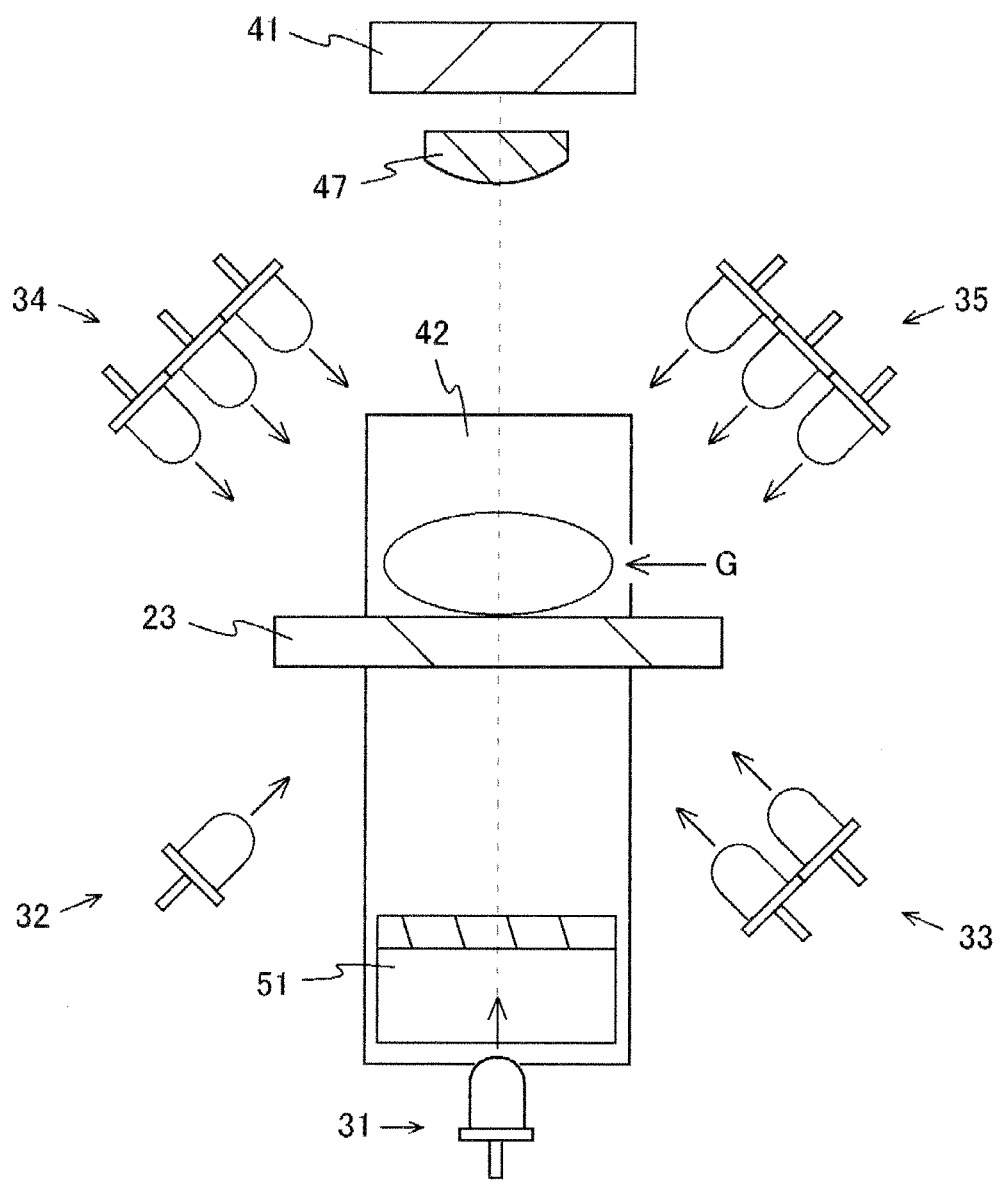
FIG. 3 is an explanatory diagram of the optical unit illustrating a schematic diagram of the B-B cross section of FIG. 1.

FIGS. 2 and 3 are explanatory diagrams of the optical unit 3 of the grain quality level discrimination device in accordance with the embodiment 1-1 of the present invention. FIG. 2 illustrates a schematic diagram of the A-A cross section of FIG. 1, and FIG. 3 illustrates a schematic diagram of the B-B cross section of FIG. 1.

According to the embodiment 1-1, the optical unit 3 has light sources 31 to 35, photosensors 41, 42, collector lenses 47, and a dichroic filter 51.

The light sources include those provided and arranged so as to face the upper surface side of the grain G (the other surface side) (hereinafter referred to as "upper-surface side light source") and those provided and arranged to face the lower surface side of the grain G (one surface side) (hereinafter referred to as "lower-surface side light source").

It should be noted that the upper and lower surface side light sources may be arranged at inverted positions with respect to the upper and lower surfaces of the grain G, so that the upper and lower surface sides may be generalized and the lower surface side thus can be referred to as the "one surface side" and the upper surface side likewise can be referred to as the "other surface side."

The upper surface side light sources include a red-green-blue light source (RGB light source) 34 the optical axis of which is inclined with respect to the plane of rotation of the disk 21 and a red-green-blue light source (RGB light source) 35 the optical axis of which is inclined with respect to the plane of rotation of the disk 21 in the opposite direction away from the RGB light source 34 (FIG. 3).

Also, the lower surface side light sources include a blue light source (B light source) 31 the optical axis of which is substantially orthogonal to the plane of rotation of the disk 21, a green light source (G light source) 32 the optical axis of which is inclined with respect to the plane of rotation of the disk 21, and a red-green light source (RG light source)

33 the optical axis of which is inclined with respect to the plane of rotation of the disk 21 in the opposite direction away from the G light source 32. The blue light source 31 emits blue light (single-color light of a wavelength range of 435 to 500 nanometers) for use in identifying the planar shape of the grain.

It should be noted that the blue light, whose absorbance of the grain G is low, is useful as a means for identifying the planar shape of the grain G (which may hereinafter be referred to as "particular light source" or "particular light").

Here, according to the present invention, red, green, and blue LEDs are respectively used as the respective light sources, but other illumination devices can also be relied on.

The photosensors includes an upper surface side photosensor 41 provided to face the upper surface of the grain G and arranged to be able to scan in parallel with the plane of rotation of the disk 21 and in the direction orthogonal to the conveying direction of the grain G, and a side surface side photosensor 42 provided to face the side surface of the grain G and arranged to be able to scan in the direction orthogonal to the plane of rotation of the disk 21 (FIG. 2).

The upper surface side photosensor 41 includes an upper surface light receiving area "a" that is positioned on the optical axis of the blue light source 31 arranged on the lower surface side and is adapted to receive the reflected and/or transmitted light from the upper surface side of the grain G.

Also, the side surface side photosensor 42 includes a lower surface light receiving area "b" that receives the reflected and/or transmitted light from the lower surface side of the grain G and a side surface side light receiving area "c" that receives the reflected and/or transmitted light from the side surface side of the grain G.

Although in the context of the present invention linear image sensors are used as the respective photosensors, other photosensors may also be used.

The collector lenses 47 may also be provided and arranged in front of the corresponding light receiving areas of the upper and side surface side photosensors 41, 42.

The dichroic filter is a dichroic short-pass filter 51 having a property of transmitting the blue light among lights of the three primary colors, i.e., red (R), green (G), and blue (B) and reflecting the green and red lights, which is arranged so as to face the lower surface side of the grain G and disposed between the grain G and the blue light source 31 on a path of the blue light from the blue light source 31 to the grain G at an angle of inclination of 45 degrees with respect to the plane of rotation of the disk 21 and the side surface side photosensor 42.

According to the grain quality level discrimination device in accordance with an embodiment 1-1 of the present invention, the grains G received respectively in the recesses 22 of the disk 21 the quality level of which should be discriminated are continuously conveyed toward the optical unit 3 by the rotation of the disk 21 of the conveying unit 2.

With regard to the optical unit 3, the upper and lower surface side light sources are alternately turned on, and the grain G conveyed toward the optical unit 3 is irradiated by the light alternately on its upper and lower surfaces of the grain G.

In addition, the upper surface light receiving area "a" of the upper surface side photosensor 41 receives the reflected and/or transmitted light from the upper surface side of the grain G.

Also, the lower surface light receiving area "b" of the side surface side photosensor 42 receives the reflected and/or transmitted light from the lower surface side of the grain G, and the side surface light receiving area "c" of the side surface side photosensor 42 receives the reflected and/or transmitted light from the side surface side of the grain G.

Here, the blue light emitted from the blue light source 31 included in the lower surface side light sources is transmitted through the dichroic short-pass filter 51.

As a result, the upper surface light receiving area "a" of the upper surface side photosensor 41 is capable of alternately receiving the transmitted blue light from the blue light source 31 necessary for identifying the planar shape of the grain G and the reflected and/or transmitted light from the upper surface side of the grain G.

Also, the dichroic short-pass filter 51 reflects to the side surface side photosensor 42 the green and red lights other than the blue one among the reflected and/or transmitted light from the lower surface side of the grain G.

As a result, the lower surface light receiving area "b" of the side surface side photosensor 42 is capable of receiving the reflected and/or transmitted light except for the blue one from the lower surface side of the grain G regardless of the presence of the blue light source in the lower surface side of the grain G.

It should be noted in FIG. 2 that it is also possible to obtain the light reception relationship as described above when the photosensor 41 is configured to include the first light receiving area "a" and the third light receiving area "c" and the photosensor 42 is configured to include the second light receiving area "b" by separating the third light receiving area "c" of the photosensor 42 and instead making it integral with the light receiving area "a" of the photosensor 41, and arranging a reflection member that reflects the reflected and/or transmitted light from the side surface side of the grain G toward the light receiving area "c".

Specifically, it will be appreciated that the particular light of a predetermined wavelength required for identifying the planar shape of the grain G transmitted through the grain G from the lower surface side can be received by the upper surface side photosensor 41 (first light receiving unit), in addition to which, on the lower surface side on which this particular light is emitted as well, the transmitted light through the grain G from the upper surface side and the reflected particular light in the lower side of the grain can be received by the lower surface side photosensor 42 (second light receiving unit). As a result, it is possible to receive at least the reflected and/or transmitted light from the upper and lower surfaces of the grain G by one single optical unit 3 simultaneously.

Accordingly, in accordance with the above-described embodiment 1-1 of the present invention, the reflected and/or transmitted light from the upper, lower, and side surfaces of the grain G are received simultaneously by one single optical unit disposed at one single location, so that it's possible to receive the reflected and/or transmitted light at the same conveying speed of the grain G without being affected by the conveying speed even when it is unstable, and make the amounts (the number of times) of the light reception signals from the upper and lower surfaces of one grain G identical with each other. The light can be received with the same state of attitude of the grain, so that it's possible to obtain the planar shape of the grain G on the upper and lower surfaces of the grain G as the data in the same attitude. Thus, the accuracy of the quality level discrimination of the grains G can be improved.

Also the grain quality level discrimination device can be miniaturized and the costs for it can also be reduced, since it's possible to receive at least the reflected and/or transmitted light from the upper and lower surfaces of grain G simultaneously by the one single optical unit 3.

Further, according to the embodiment 1-1, the reflected and/or transmitted light from three directions, i.e. from the upper, lower, and side surface sides of the grain G can be received by not three but two sensors, which leads to cost reduction.

Embodiment 1-2

Figure 4:
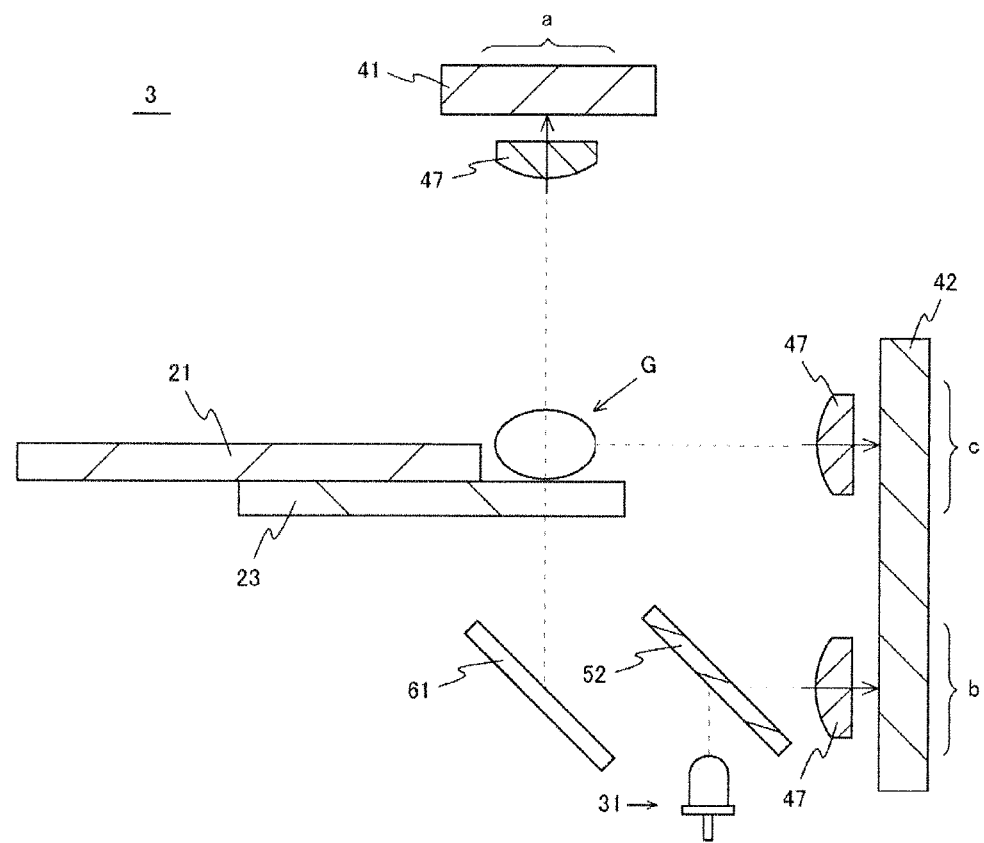
FIG. 4 is an explanatory diagram of an optical unit in accordance with an embodiment 1-2 of the present invention.

FIG. 4 illustrates an explanatory diagram of an optical unit in accordance with an embodiment 1-2 of the present invention.

According to this embodiment, a dichroic long-pass filter 52 used as the dichroic filter has a property of reflecting blue light among lights of the three primary colors, i.e., red (R), green (G), and blue (B) colors and transmitting the green and red lights.

The dichroic long-pass filter 52 is disposed in the lower surface side of the grain G between the grain G and the blue light source 31 at an angle of inclination of 45 degrees with respect to the plane of rotation of the disk 21 and the side surface side photosensor 42.

A reflection member 61 is also provided and arranged between the grain G and the dichroic long-pass filter 52 in parallel with the filter 52.

Here, although a mirror is used as the reflection member 61 in accordance with the present invention, other components can also be used therefor.

The remaining features are identical with those in the embodiment 1, whose explanations are not repeated here.

According to the embodiment 1-2 of the present invention as well, the upper surface light receiving area "a" of the upper surface side photosensor 41 receives the reflected and/or transmitted light from the upper surface of the grain G.

Also, the lower surface light receiving area "b" of the side surface side photosensor 42 receives the reflected and/or transmitted light from the lower surface side of the grain G, and the side surface light receiving area "c" of the side surface side photosensor 42 receives the reflected and/or transmitted light from the side surface side of the grain G.

The dichroic long-pass filter 52 reflects the blue light from the blue light source 31 to the reflection member 61 and the reflection member 61 in turn reflects the blue light reflected from the dichroic long-pass filter 52 toward the lower surface side of the grain G.

As a result, the upper surface light receiving area "a" of the upper surface side photosensor 41 is capable of receiving the reflected and/or transmitted light from the upper surface of the grain. G including the transmitted blue light required for identifying the planar shape of the grain G.

The green and red lights except for the blue light among the reflected and/or transmitted light from the lower surface side of the grain G are reflected by the reflection member 61, and then transmitted through the dichroic long-pass filter 52.

As a result, the lower surface light receiving area "b" of the side surface side photosensor 42 can receive the reflected and/or transmitted light except for the blue light from the lower surface side of the grain G.

Accordingly, in accordance with the above-described embodiment 1-2 of the present invention as well, it is possible to receive the reflected and/or transmitted light from the upper, lower, and the side surface sides of the grain G simultaneously by one single optical unit 3.

Embodiment 1-3

Figure 5:
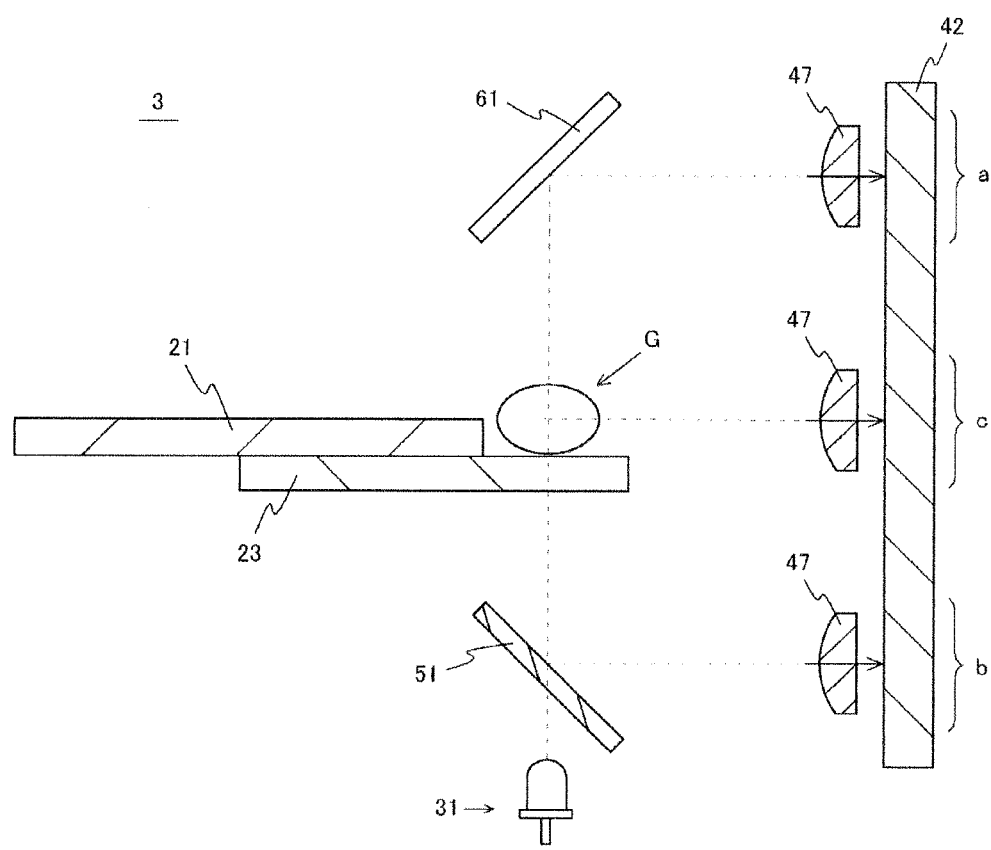
FIG. 5 is an explanatory diagram of an optical unit in accordance with an embodiment 1-3 of the present invention.

FIG. 5 illustrates an explanatory diagram of an optical unit in accordance with an embodiment 1-3 of the present invention.

The optical unit 3 in accordance with the embodiment 1-3 of the present invention differs from the optical unit 3 of the embodiment 1 in that the photosensor only includes the side surface side photosensor 42 arranged in the side surface side of the grain G so as to be able to scan in the direction orthogonal to the plane of rotation of the disk 21 of the conveying unit 2.

The side surface side photosensor 42 includes a upper surface light receiving area "a" for receiving the reflected and/or transmitted light from the upper surface side of the grain G, a lower surface light receiving area "b" for receiving the reflected and/or transmitted light from the lower surface side of the grain G, and a side surface light receiving area "c" for receiving the reflected and/or transmitted light from the side surface side of the grain G.

Also, according to the embodiment 1-3 of the present invention, the reflection member 61 is provided and arranged in the upper surface side of the grain G so as to reflect the reflected and/or transmitted light from the upper surface side of the grain G toward the upper surface light receiving area "a".

Accordingly, in accordance with the above-described embodiment 1-3 of the present invention as well, it's possible to receive the reflected and/or transmitted light from the upper, lower, and side surface sides of the grain G simultaneously by one single optical unit.

According to the embodiment 1-3 of the present invention, it's possible to receive the reflected and/or transmitted light from three directions, i.e., from the upper, lower, and side surface sides of the grain G, by one single photosensor, so that further cost reduction can be achieved.

Embodiment 1-4

Figure 6:
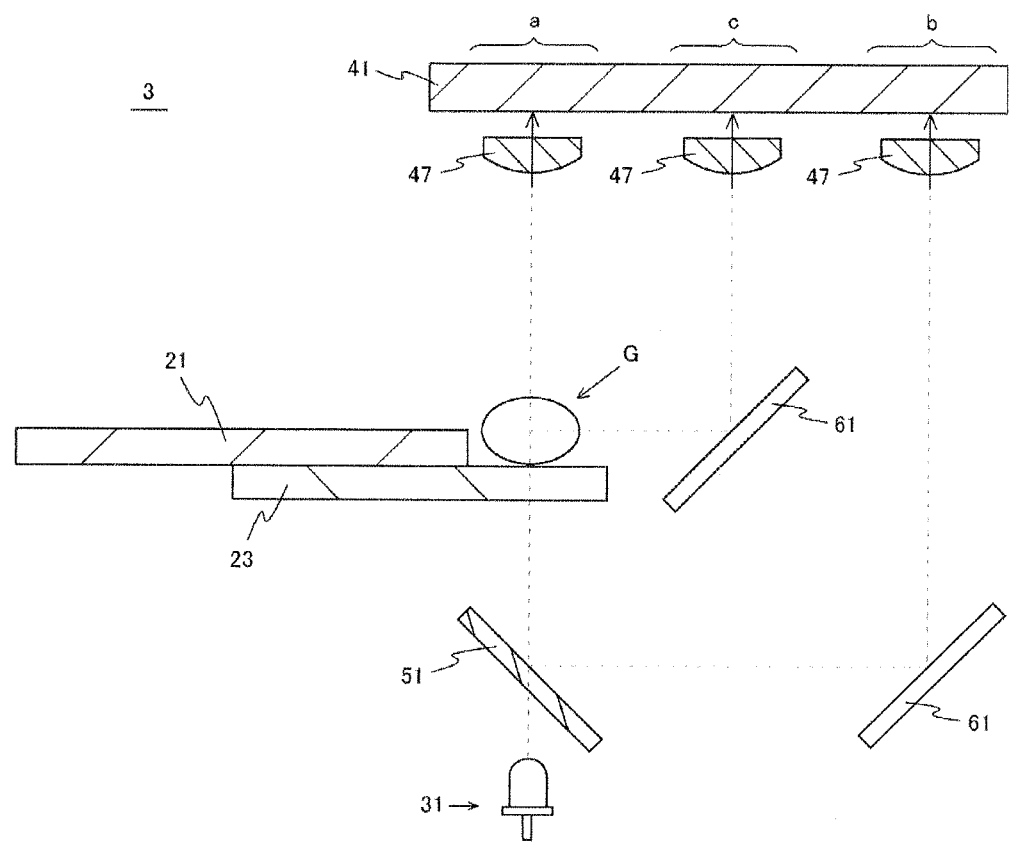
FIG. 6 is an explanatory diagram of an optical unit in accordance with an embodiment 1-4 of the present invention.

FIG. 6 illustrates an explanatory diagram of an optical unit in accordance with an embodiment 1-4 of the present invention.

The optical unit 3 in accordance with the embodiment 1-4 of the present invention differs from the optical unit 3 of the embodiment 1-3 in that the photosensor only includes the upper surface side photosensor 41 arranged in the upper surface side of the grain G so as to be able to scan in parallel with the plane of rotation of the disk 21 of the conveying unit 2 and in the direction orthogonal to the conveying direction of the grain G.

The photosensor 41 in the upper surface side includes an upper surface light receiving area "a" for receiving the reflected and/or transmitted light from the upper surface side of the grain G, a lower surface light receiving area "b" for receiving the reflected and/or transmitted light from the lower surface side of the grain G, and a side surface light receiving area "c" for receiving the reflected and/or transmitted light from the side surface side of the grain G.

In accordance with the embodiment 1-4 of the present invention, a reflection member 61 is provided and arranged in the lower surface side of the grain G for reflecting the reflected and/or transmitted light from the lower surface side of the grain G toward the lower surface light receiving area "b", and another reflection member 61 is also provided for reflecting the reflected and/or transmitted light from the side surface side of the grain G toward the side surface light receiving area "c".

Accordingly, in accordance with the above-described embodiment of the present invention 4 as well, the reflected and/or transmitted light from the upper, lower, and side surface sides of the grain G can be simultaneously received by one single optical unit.

According to the above-described embodiment 1-4 of the present invention as well, it's possible to receive the reflected and/or transmitted light from three directions, i.e. from the upper, lower, and side surface sides of the grain G by single photosensor, so that further cost reduction can be achieved.

Embodiment 1-5

Figure 7:
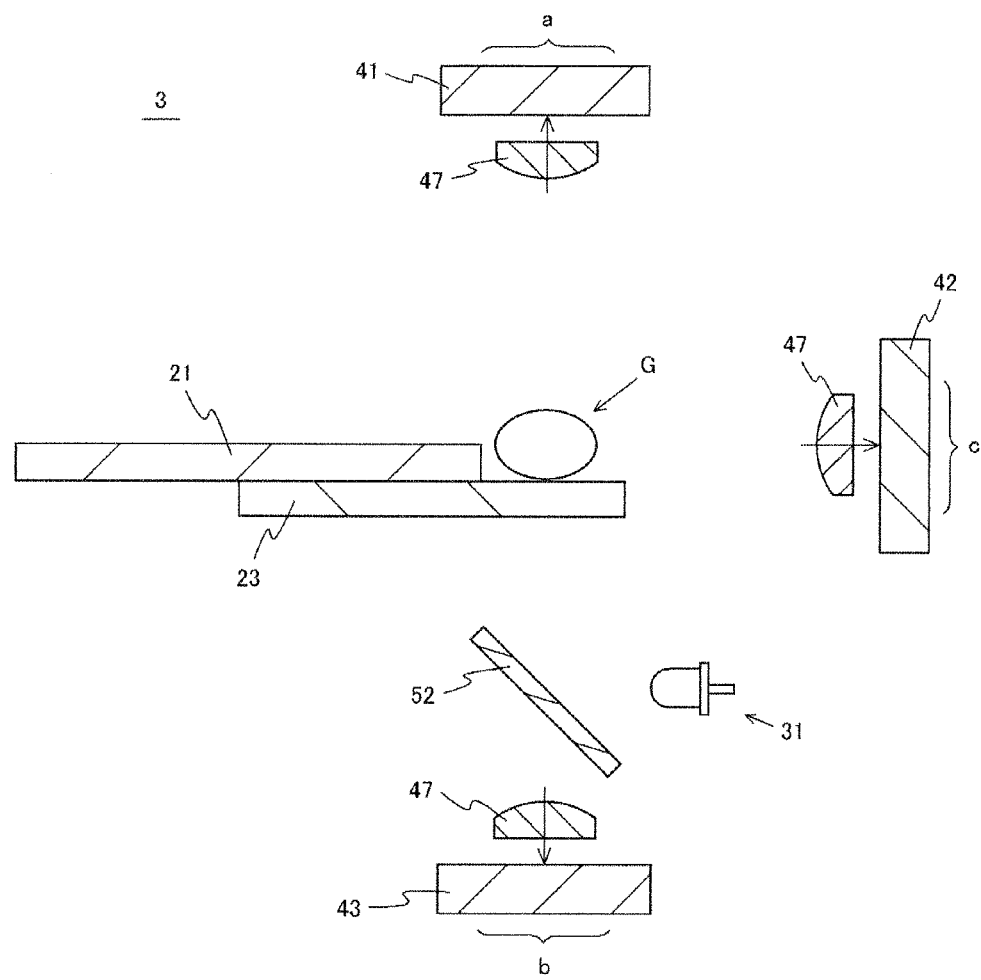
FIG. 7 is an explanatory diagram of an optical unit in accordance with an embodiment 1-5 of the present invention.
Figure 8:
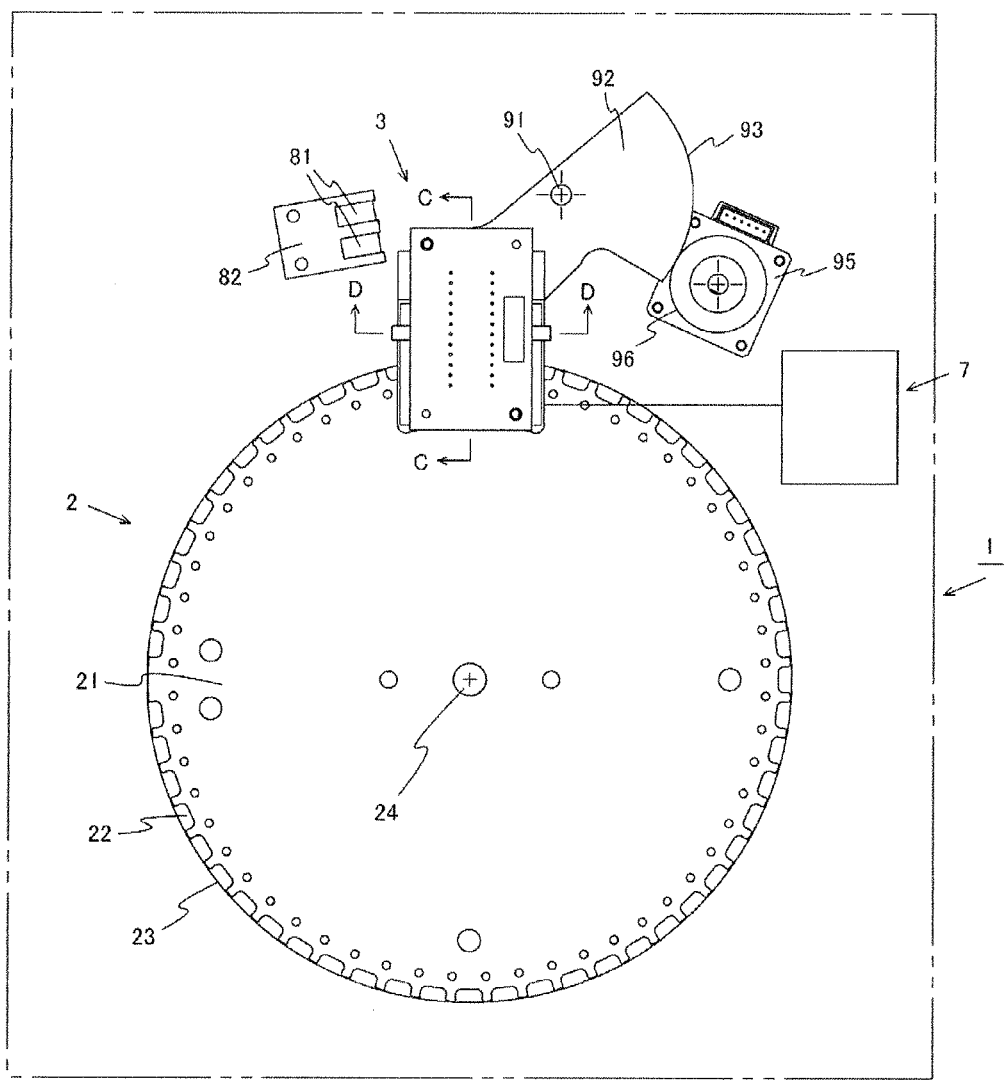
FIG. 8 is a schematic explanatory diagram of a grain quality level discrimination device in accordance with an embodiment 2 of the present invention illustrating a conveying unit, an optical unit, a quality level discrimination unit, and a reference plate in a schematic plan view.

FIG. 7 illustrates an explanatory diagram of an optical unit in accordance with an embodiment 1-5 of the present invention.

The optical unit 3 in accordance with the embodiment 1-5 of the present invention differs from that of the embodiment 1-1 in that the dichroic filter is configured as a dichroic long-pass filter 52, and in that the location of blue light source 31 and that of the lower surface light receiving area "b" are interchanged.

Specifically, the optical unit 3 in accordance with the embodiment 1-5 is of the configuration such that the blue light source 31 is provided and arranged at the position where the lower surface light receiving area "b" of the side surface side photosensor 42 in accordance with the embodiment 1-1 should be arranged, and the lower surface side photosensor 43 including the lower surface light receiving area "b" for receiving the reflected and/or transmitted light from the lower surface side of the grain G is arranged at the position where the blue light source 31 in accordance with the embodiment 1-1 should be arranged.

Accordingly, in accordance with the above-described embodiment 5 of the present invention as well, the reflected and/or transmitted light from the upper, lower, and side surface sides of the grain G can be simultaneously received by one single optical unit.

Although the blue light is used as the light for identifying the planar shape of the grain G in accordance with the above-described embodiments of the present invention, other monochromatic light can be used as long as they can identify the planar shape of the grain G. Also, they are not limited to those of single colors, and other light combining multiple colors such as "blue+red," "blue+green," "red+green," "blue+red+green," and so forth can also be used and visible rays of light of colors other than red, blue, and green can also be used.

Although the dichroic filter is used in the above-described embodiments of the present invention, other optical filters can also be used as long as they can transmit or reflect a particular light such as blue light while it reflects or transmits other lights of other wavelengths.

It should be noted that the grain quality level discrimination devices in accordance with the respective embodiments 1-1 to 1-5 are configured to receive the reflected and/or transmitted light simultaneously from the upper, lower, and side surface sides of the grain G by one single optical unit, but it should at least be configured to receive the reflected and/or transmitted light simultaneously from the upper and lower surface sides of grain G by one single optical unit.

Embodiment 2

A grain quality level discrimination device 1 in accordance with an embodiment 2 includes, in addition to the features of the embodiment 1, a reference plate 81 for correction of an amount of light received by the photosensor of the optical unit 3. Also, the reference plate 81 is mounted on a holding member 82 provided at a position different from that of the disk 21 of the conveying unit 2 and arranged so as to be away from the disk 21 of the conveying unit 2. As a result, the grain quality level discrimination device 1 in accordance with the embodiment 2 includes a mechanism that moves the optical unit 3 between a position facing the grain G and a position facing the reference plate 81.

Figure 9:
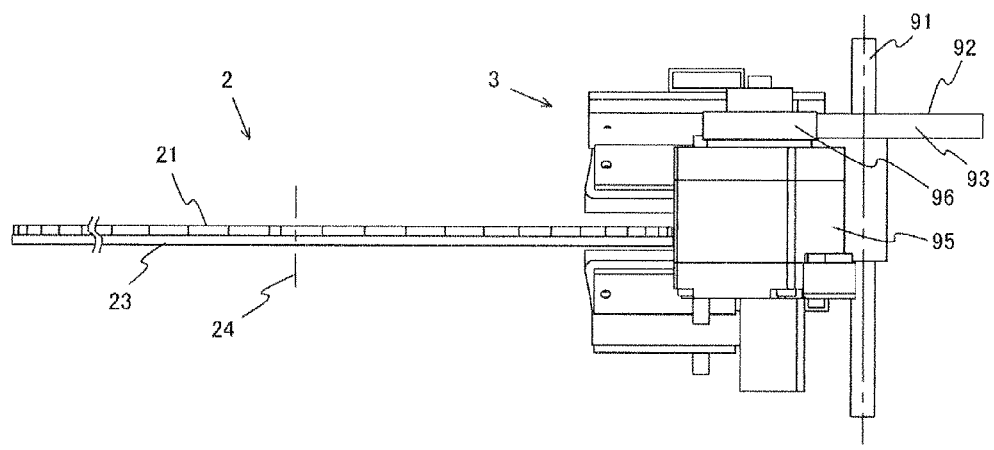
FIG. 9 is a schematic explanatory diagram of a grain quality level discrimination device in accordance with an embodiment of the present invention illustrating a schematic right side view of a conveying unit and an optical unit.
Figure 10:
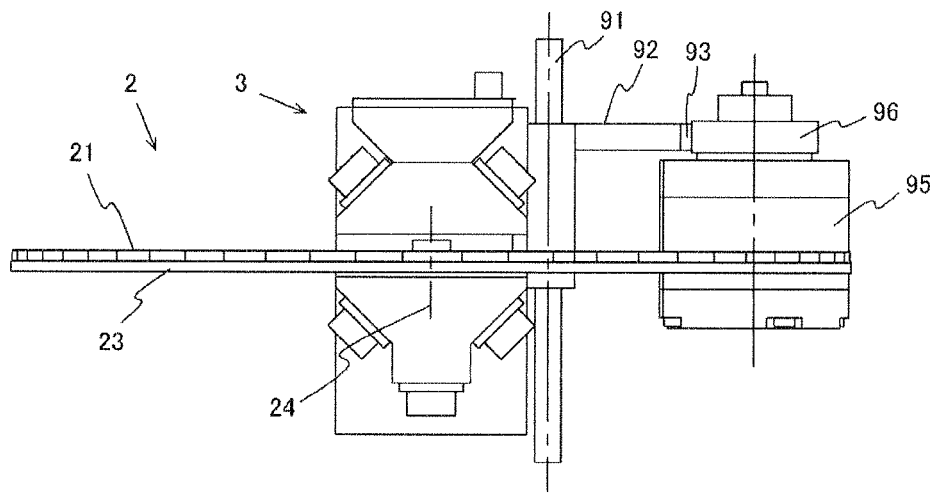
FIG. 10 is a schematic explanatory diagram of a grain quality level discrimination device in accordance with an embodiment of the present invention illustrating a schematic front view of a conveying unit and an optical unit.

Specifically, the optical unit 3 is secured to a rotating member 92 that is adapted to be pivotable about a shaft 91 (FIGS. 9, 10) arranged in parallel with the rotation shaft 24 of the disk 21. The rotating member 92 has an arc-shaped outer peripheral edge, and a gear 93 is formed on the side surface of the outer peripheral edge which is adapted to be engaged with a gear 96 that transmits a rotational driving force of a motor 95 arranged adjacent to the rotating member 92.

The grain quality level discrimination device 1 in accordance with the embodiment 2 has the same features as those of the embodiment 1 with regard to the conveying unit 2 that conveys the grain G, the optical unit 3 that emits light to the grain G and receives the reflected and/or transmitted light from the grain G, and the quality level discrimination unit 7 for discriminating the quality level of the grain G. The conveying unit 2 is a disk 21 rotationally driven by a not-shown driving motor, numerous recesses 22 are formed on its peripheral edge, and a transparent bottom plate 23 is provided in each recess 22.

The optical unit 3 has light sources for irradiating the grain G, and sensors for receiving the reflected and/or transmitted light from the grain G. The grains G supplied onto the disk 21, conveyed continuously by the rotation thereof, and received respectively in each recess 22 of the disk 21 are irradiated by the light sources, then the reflected and/or transmitted light from the grain G is received by the photosensor, and thus the light reception signals are obtained. In addition, the quality level discrimination unit 7 discriminates the quality level of the grain G on the basis of the light reception signal obtained by the optical unit 3.

The grain quality level discrimination device 1 in accordance with the embodiment 2 further includes the reference plate 81 for correction of the amount of light received in the photosensor of the optical unit 3.

The reference plate 81 is mounted on the holding member 82 provided at a position different from that of the disk 21 of the conveying unit 2 so as to be away from the disk 21 of the conveying unit 2.

A pair of plates different in their gray levels or the like such as white and milky white plates are used as the reference plate 81, but three or more plates may also be used.

Figure 11:
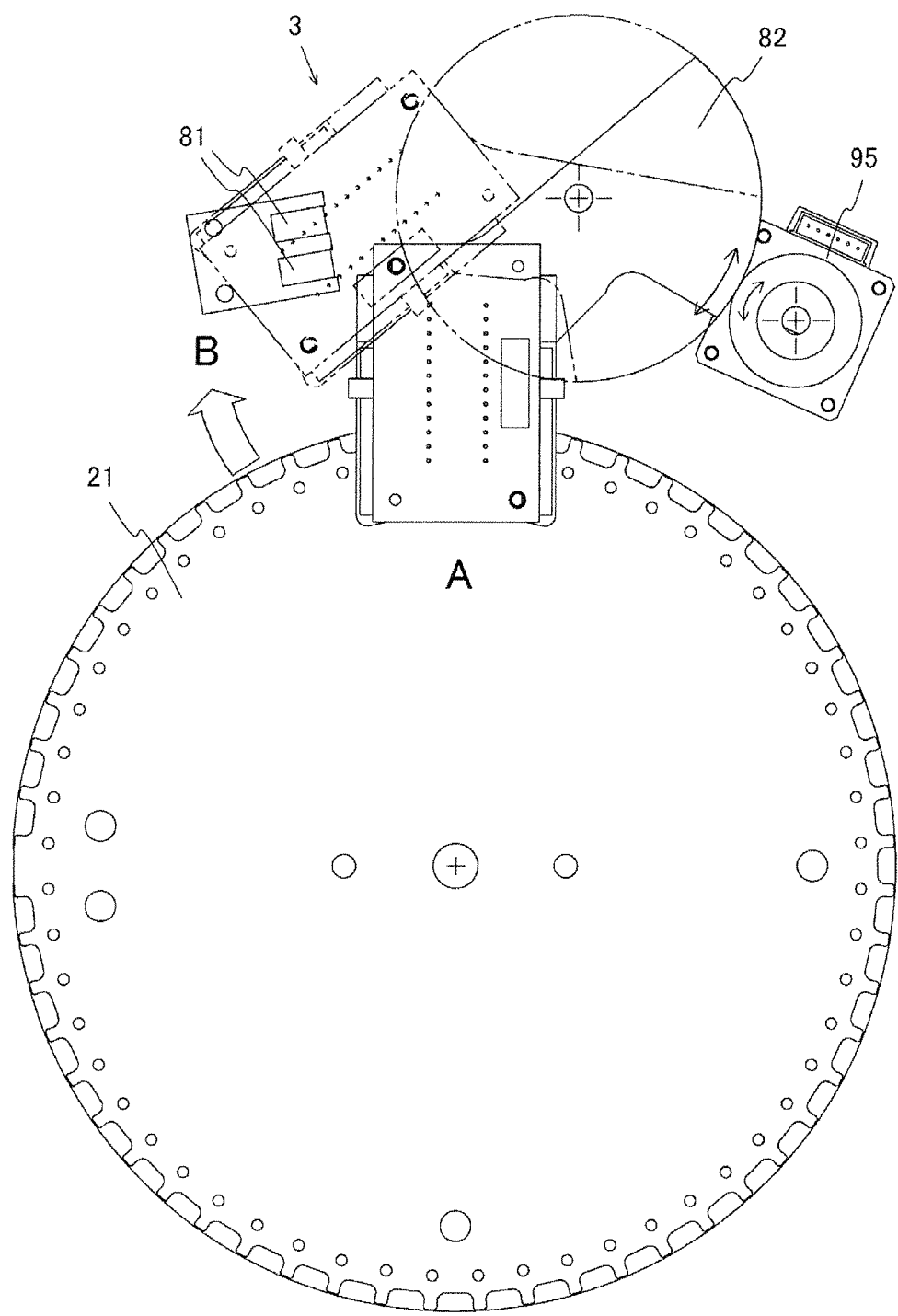
FIG. 11 is an explanatory diagram of the grain quality level discrimination device in accordance with an embodiment of the present invention, where the optical unit is to be shifted.

FIG. 11 is an explanatory diagram of a case where the optical unit 3 is shifted pivotably in the grain quality level discrimination device 1 in accordance with the embodiment 2.

The optical unit 3 can be shifted between a grain measurement position A on the disk 21 (first position) and a reference plate position B (second position) different from the first position by pivotably shifting the member 92 by means of the rotational driving of the motor 95. In the reference plate position B the optical unit 3 is positioned away from the disk 21.

At the reference plate position B, the light source of the optical unit 3 of the grain quality level discrimination device 1 emits light to the reference plate 81, the reflected and/or transmitted light from the reference plate 81 is received by the photosensor of the optical unit 3, the amount of thus received light is compared with a predefined reference quantity of light, and a correction coefficient for correction of the amount of light received by the photosensor is calculated.

At the grain measurement position A, the light source of the optical unit 3 of the grain quality level discrimination device 1 emits light to the grain G accommodated in the recess 22 of the disk 21, the reflected and/or transmitted light from the grain G is received by the photosensor of the optical unit 3, and then corrects the amount of light received by the photosensor by multiplying it by the correction coefficient.

The grain quality level discrimination device 1 in accordance with the embodiment 2 has the reference plate 81 that is mounted on the holding member 82 provided at a position different and away from that of the disk 21 of the conveying unit 2, and the optical unit 3 that is arranged to be able to shift pivotably between the grain measurement position A on the disk 21 and the reference plate position B that provided at a position away from and different from that of the disk 21, so that scratches and stains on the reference plate 81 due to contact with the grains G or the like supplied on the disk 21 hardly occurred. As a result, the accuracy of the quality level discrimination of the grain G is not degraded. Also, even when the reference plate 81 is damaged, broken pieces of it will not be mixed into the grains G supplied on the disk 21.

In the grain quality level discrimination device 1 of the embodiment 2, scratches and/or stains are prevented from created on the reference plate 81 due to the contact with the grains G or the like supplied onto the disk 21, so that the frequency of replacement of the reference plate is remarkably decreased when compared with conventional ones, and the operations associated therewith and the burden of the operations associated with setting the reference quantity of light accompanied with the replacement of the reference plate are remarkably reduced.

Further, in the grain quality level discrimination device 1 of the embodiment 2, since the replacement frequency of the reference plate 81 is remarkably decreased, the device 1 is less susceptible to the differences of the individual reference plates 81, and the accuracy of the quality level discrimination of the grain G becomes stable.

In the grain quality level discrimination device 1 of the embodiment 2, the optical unit 3 pivots about the shaft 91 that is parallel with the rotation shaft 24 of the disk 21, so that it moves in parallel with the plane of rotation of the disk 21.

As a result, the positional relationship between the optical unit 3 and the grain G at the grain measurement position A that between the optical unit 3 and the reference plate 81 at the reference plate position B can be made identical with each other, so that it's possible to accurately calculate the correction coefficient for correcting the amount of light received by the photosensor.

In other words, it is desirable that the optical unit is provided and arranged such that the distance between the light source and the grain G at the first position and that between the light source and the reference plate at the second position are identical with each other, and it is also desirable that the optical unit is provided and arranged such that the distance between the photosensor and the grain G at the first position and that between the photosensor and the reference plate at the second position are identical with each other.

When the correction coefficient is to be calculated for each light of the three primary colors, i.e., red light, green light, and blue light, then the accuracy of the quality level discrimination of the grain G will further be enhanced.

In accordance with the embodiment 2, when the grain G is to be measured, the grain G is conveyed at a predetermined conveying speed relative to the optical unit 3 by the disk 21. Accordingly, when the reference plate 81 is to be measured, it should be ensured that the reference plate 81 is allowed to be conveyed at the same speed relative to the optical unit 3 as the conveying speed. As the method of conveyance, by way of example, it should be ensured that, at the reference plate position B, the holding member 82 is rotated in the same manner as the disk 21, and, with regard to the optical unit 3, then the reference plate 81 should be conveyed at the conveying speed. Alternatively, adjusting the speed of the optical unit 3 on the rotation, the reference plate 81 should be conveyed at substantially the same speed as the conveying speed relative to the optical unit 3.

It should be noted that, the optical unit may be configured to be linearly moved between the first position and the second position.

Embodiment 3

In a grain quality level discrimination device 1 in accordance with an embodiment 3 as well, in the same manner as in the embodiment 2 that has been illustrated in FIG. 11, the optical unit 3 is adapted to be pivoted by means of the rotational driving of the motor 95 and via the rotating member 92, between the grain measurement position A on the disk 21 and the reference plate position B away from the disk 21 and is different from the grain measurement position A (FIG. 11 should also be read in the context of the embodiment 3).

At the reference plate position B, the light source of the optical unit 3 of the grain quality level discrimination device 1 emits light to the upper and lower-surfaces of the reference plate 81, the reflected and/or transmitted light from the upper and lower surfaces of the reference plate 81 are received respectively by the photosensor of the optical unit 3, the respective amount of thus received light is compared with a predefined reference quantity of light, then the correction coefficients for correction of the respective amounts of light received by the photosensor is calculated.

Then the light source of the optical unit 3 of the grain quality level discrimination device 1 emits light to the side-surface reference plate 84, the reflected and/or transmitted light from the side surface of the side-surface reference plate 84 is received by each photosensor of the optical unit 3, the amount of thus received light from the side surface is compared with the predefined reference quantity of light, and the correction coefficient for correction of the amount of light received by the photosensor is calculated.

At the grain measurement position A, the light source of the optical unit 3 of the grain quality level discrimination device 1 emits light to the grain G received in the recess 22 of the disk 21, the reflected and/or transmitted light from the upper, lower, and side surface sides of the grain G is received by the photosensor of the optical unit 3, and the respective amounts of thus received light is corrected by multiplying the respective correction coefficients with the respective amounts of received light.

Specifically, in accordance with the embodiment 3, two reference plates 81, 84 are mounted on the holding member 82. One is an upper/lower-surface reference plate 81 for correction of the amount of the reflected and/or transmitted light received from the upper and/or lower surfaces of the grain G by the photosensor, and the other is a side-surface reference plate 84 for correction of the amount of the reflected and/or transmitted light received from the side surface of the grain G by the photosensor.

It should be noted that, as the upper/lower-surface reference plate 81, two types of reference plates different in their levels of brightness (gray levels), for example, two reference plates including white first reference plate and semi-transparent second reference plate, may be used. In that case, three reference plates will be mounted on the holding member 82.

In accordance with the embodiment 3, when the grain G is to be measured, the grain G is conveyed at a predetermined speed relative to the optical unit 3 by the disk 21. Accordingly, when the reference plates 81, 84 are to be measured, the reference plates 81, 84 are to be moved at the same speed as the conveying speed relative to the optical unit 3, the conveyance method of which is the same as that in the embodiment 2.

It should be noted that, in the grain quality level discrimination device in accordance with the embodiment of the present invention, when the correction coefficient is to be calculated for each light of three primary colors, i.e. the red light, the green light, and the blue light, then the accuracy of the quality level discrimination of the grain G can be further increased.

The optical unit 3 has the light sources 31 to 35, the photosensors 41, 42, the collector lenses 47, and the dichroic short-pass filter 51 (FIGS. 2,3) in the same manner as in the embodiment 1.

The upper surface side light sources arranged on the upper surface side of the grain G are two red-green-blue light sources (RGB light sources) 34, 35, and the lower surface side light sources arranged on the lower surface side of the grain G are a blue light source (B light source) 31, a green light source (G light source) 32, and a red-green light source (RG light source) 33.

The upper surface side photosensor 41 arranged in the upper surface side of the grain G in parallel with the plane of rotation of the disk 21 is arranged such that it is able to scan in the direction orthogonal to the conveying direction of the grain G, and the side surface side photosensor 42 arranged in the side surface side of the grain G and to be vertical to the plane of rotation of the disk 21 is arranged such that it is capable of scanning in the direction orthogonal to the plane of rotation of the disk 21.

The upper surface side photosensor 41 is positioned on the optical axis of the blue light source 31 and includes a upper surface light receiving area "a" receiving the reflected and/or transmitted light from the upper surface side of the grain G.

Also, the side surface side photosensor 42 includes a lower surface light receiving area "a" receiving the reflected and/or transmitted light from the lower surface side of the grain G and a side surface side light receiving area "b" receiving the reflected and/or transmitted light from the side surface side of the grain G.

Each collector lens 47 is arranged respectively in front of the light-receiving areas of the upper and side surface side photosensors 41, 42.

The dichroic short-pass filter 51 has a property of transmitting blue light among the lights of the three primary colors, i.e. red (R), green (G), and blue (B) lights while reflecting the green and red lights, and is provided and arranged so as to face the lower surface side of the grain G and disposed between the grain G and the blue light source 31 at an angle of inclination of 45 degrees with respect to the plane of rotation of the disk 21 and the second photosensor 42.

With regard to the optical unit 3, the upper and lower surface side light sources are alternately turned on at the grain measurement position A, and the light is emitted to the grain G alternately through the upper and lower surface side.

Accordingly, the upper surface light receiving area "a" of the upper surface side photosensor 41 receives the reflected and/or transmitted light from the upper surface side of the grain G, the lower-surface light receiving area "a" of the side surface side photosensor 42 receives the reflected and/or transmitted light from the lower surface of the grain G, and the side-surface light receiving area "b" of the side-surface photosensor 42 receives the reflected and/or transmitted light from the side surface of the grain G.

At the reference plate position B, the upper and lower surface side light sources of the optical unit 3 are for example turned alternately on and the respective reference plates 81, 84 are irradiated alternately from the upper and lower surface side.

Specifically, the upper surface light receiving area "a" of the upper surface side photosensor 41 receives the reflected and/or transmitted light from the upper surface side of the upper/lower surface reference plate 81, and the lower surface light receiving area "a" of the side surface side photosensor 42 also receives the reflected and/or transmitted light from the lower surface side of the upper/lower surface reference plate 81, and the side surface light receiving area "b" of the side surface side photosensor 42 receives the reflected and/or transmitted light from the side surface side of the side surface reference plate 84.

Figure 12:
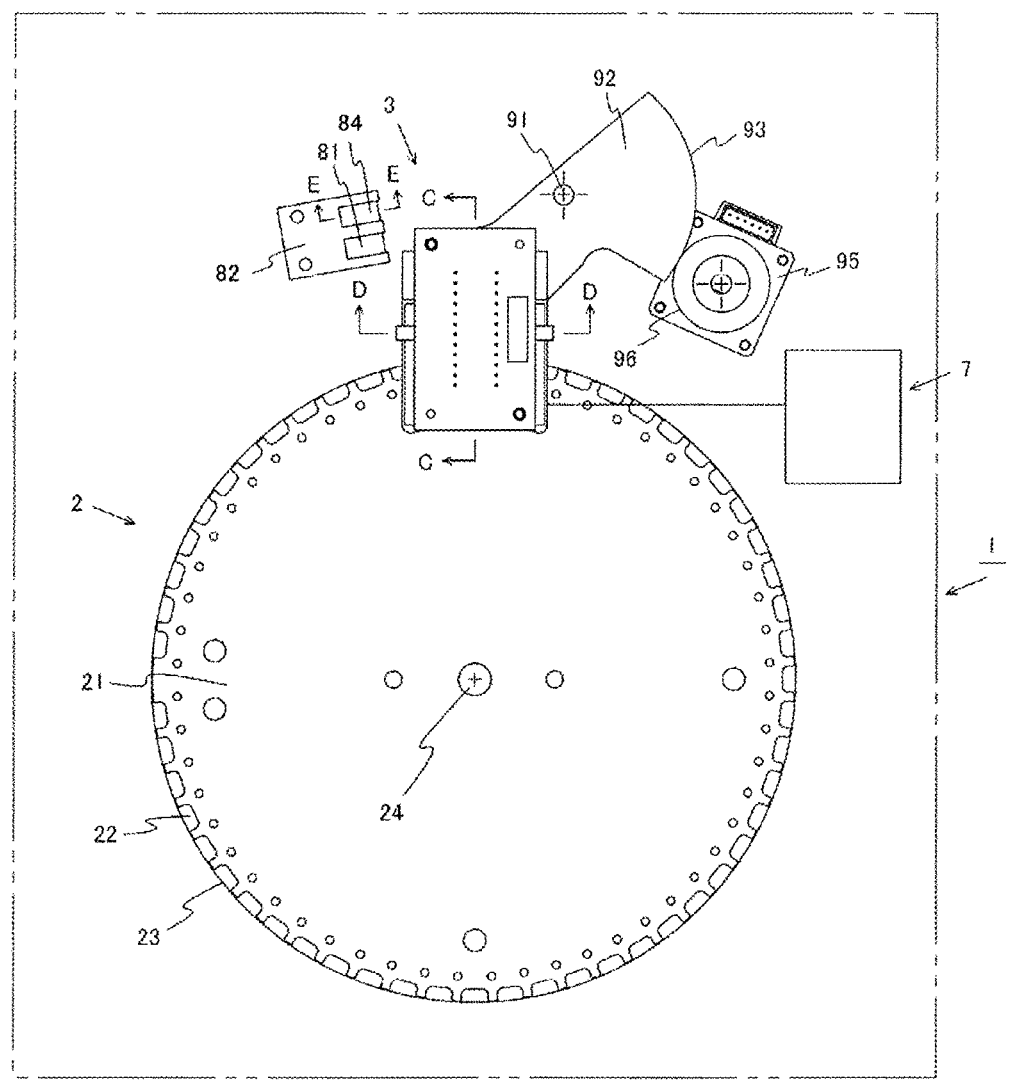
FIG. 12 is a schematic explanatory diagram of a grain quality level discrimination device in accordance with an embodiment 3 of the present invention illustrating a conveying unit, an optical unit, a quality level discrimination unit, and a reference plate in a schematic plan view.

FIGS. 13 to 18 are explanatory diagrams of the side surface reference plate 84 viewed from the cross section E-E of FIG. 12, and illustrated is the light emitted from the upper surface side light source 63 and/or the lower surface light source 62, reflected by the side surface of the side surface reference plate 84 or transmitted therethrough, and received by the light receiving area of the side surface side photosensor 65.

The upper surface side light sources 63 are the RGB light sources 34, 35 of FIG. 3, and the lower surface side light sources 62 are the B light source 31, the G light source 32, and the RG light source 33 of the same figure. Also, the side surface side photosensor 65 corresponds to the side-surface light receiving area "b" of the side surface side photosensor 42.

Figure 13:
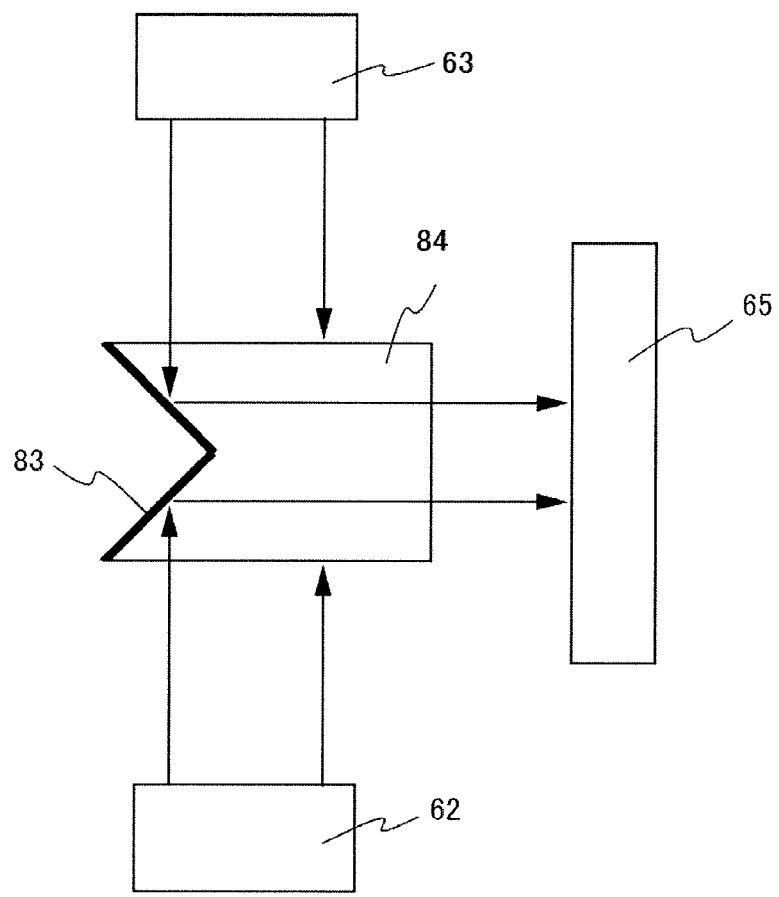
FIG. 13 is an explanatory diagram of the side-surface reference plate viewed from the C-C cross section of FIG. 12.

The side-surface reference plate 84 illustrated in FIG. 13 has a recess having a pair of vertically symmetrical linear sloping surfaces at the side surface opposite to that facing the side surface side photosensor 65, and the sloping surfaces are configured as reflection surfaces 83 for reflecting sideways the light emitted from the upper surface side light source 63 and/or the lower surface side light source 62.

Figure 14:
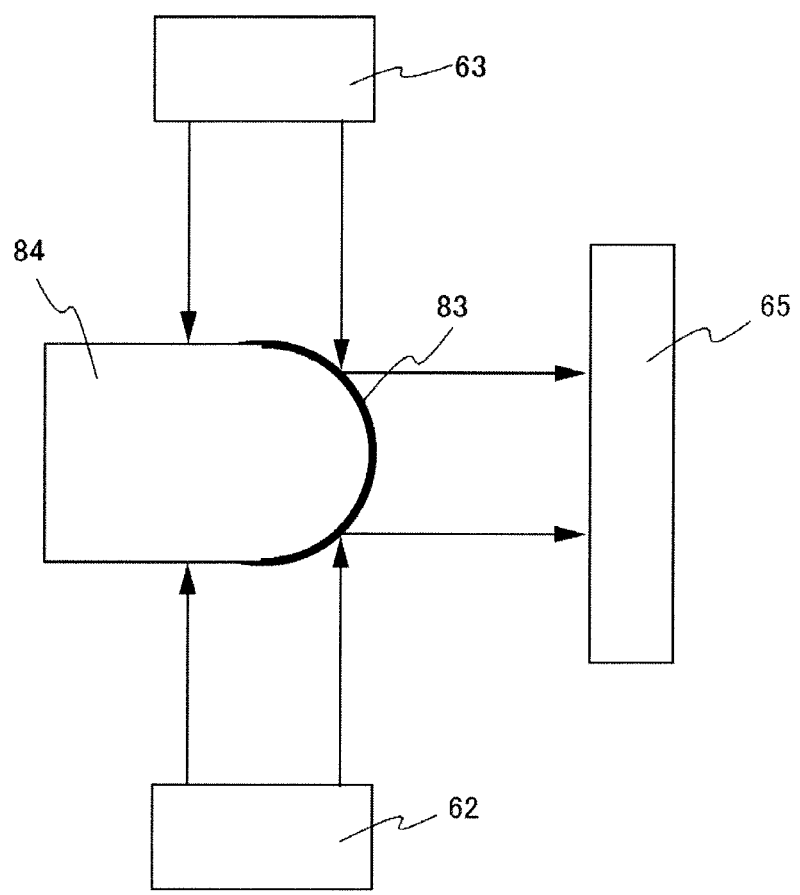
FIG. 14 is an explanatory diagram of another side-surface reference plate.

The side-surface reference plate 84 illustrated in FIG. 14 is formed with a convex portion having a vertically symmetrical arc-like sloping surface on the side surface facing the side surface side photosensor 65. The sloping surface is configured as a reflection surface 83 for reflecting sideways the light emitted from the upper surface side light source 63 and/or the lower surface side light source 62.

Figure 15:
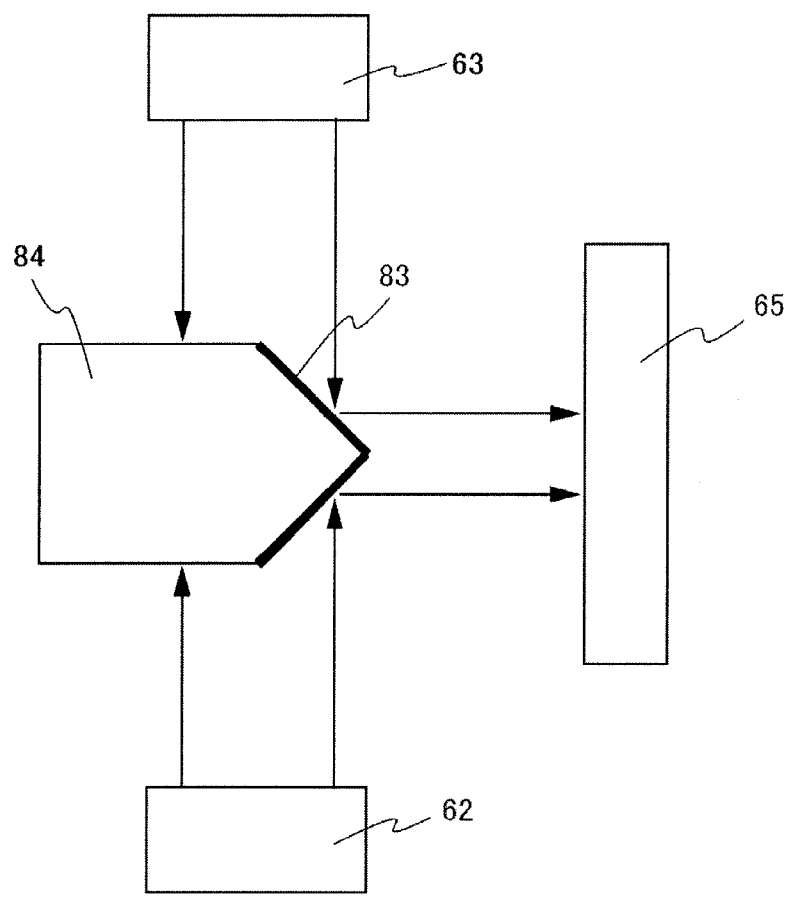
FIG. 15 is an explanatory diagram of another side-surface reference plate.

The side-surface reference plate 84 illustrated in FIG. 15 is formed with a convex portion having a vertically symmetrical linear sloping surface on the side surface facing the side surface side photosensor 65. The the sloping surface is configured as a reflection surface 83 for reflecting sideways the light emitted from the upper surface side light source 63 and/or the lower surface side light source 62.

Figure 16:
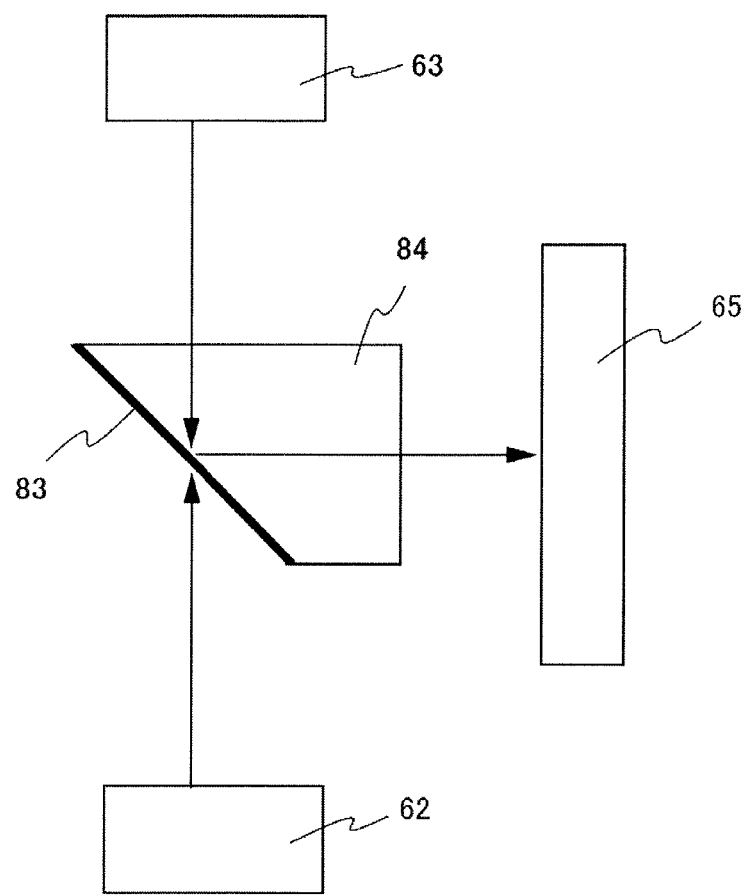
FIG. 16 is an explanatory diagram of another side-surface reference plate.

The side-surface reference plate 84 illustrated in FIG. 16 is formed with a linear downwardly sloping surface on the side surface that is the opposite to that facing the side surface side photosensor 65. The sloping surface is configured as a reflection surface 83 for reflecting sideways the light emitted from the upper surface side light source 63 and/or the lower surface side light source 62.

It should be understood that the side-surface reference plates 84 illustrated in FIGS. 13 to 16 can be used in a left and right reversed state.

Also, the side-surface reference plate 84 illustrated in FIG. 16 can be used in an upside down state.

Further, the side-surface reference plate 84 is not limited to those described with reference to FIGS. 13 to 16, and it might be the one including a reflection surface for reflecting sideways the light emitted from the upper surface side light source 63 and/or the lower surface side light source.

It is easy to produce the side-surface reference plate 84 illustrated in FIG. 16 since only a linear sloping surface might be formed.

A pair of side-surface reference plates 84 are illustrated in FIG. 16 in the left and right reversed or upside down states.

Figure 17:
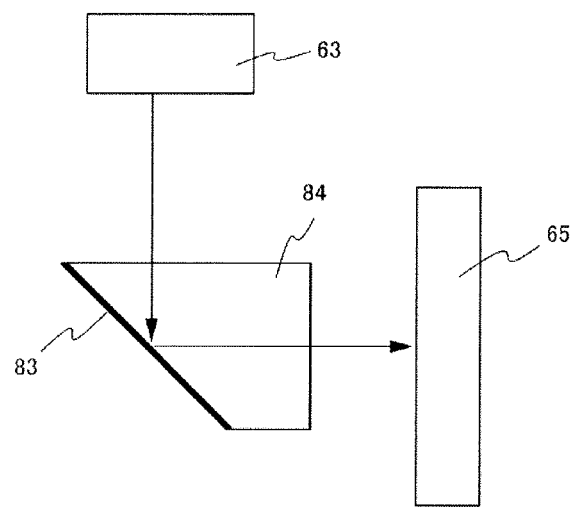
FIG. 17 is an explanatory diagram of another side-surface reference plate.
Figure 17:
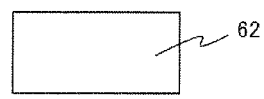
Figure 17:
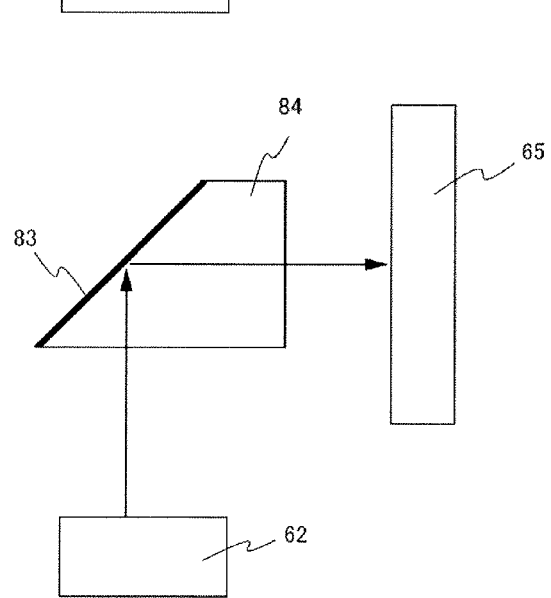

FIG. 17 illustrates an example where a pair of side-surface reference plates 84 of FIG. 16 are used in the upside down state.

In FIG. 17(*a*), the light emitted from the upper surface side light source 63 is reflected sideways by the downwardly facing reflection surface 83 of the side-surface reference plate 84, and in FIG. 17(*b*) the light reflected from the lower surface side light source 62 is reflected sideways by the upwardly facing reflection surface 83 of the side-surface reference plate 84.

Figure 18:
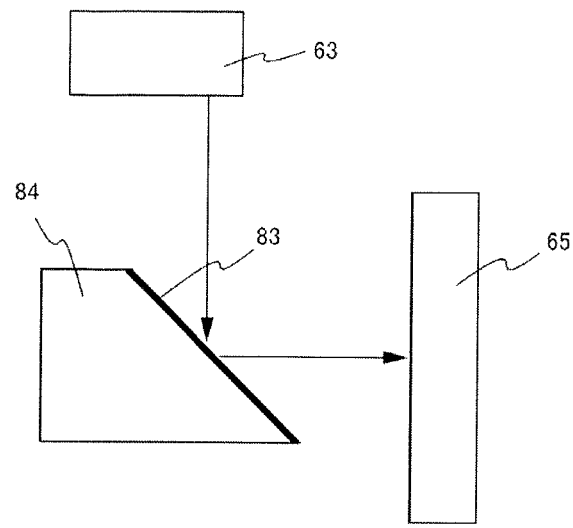
FIG. 18 is an explanatory diagram of another side-surface reference plate.
Figure 18:
Figure 18:
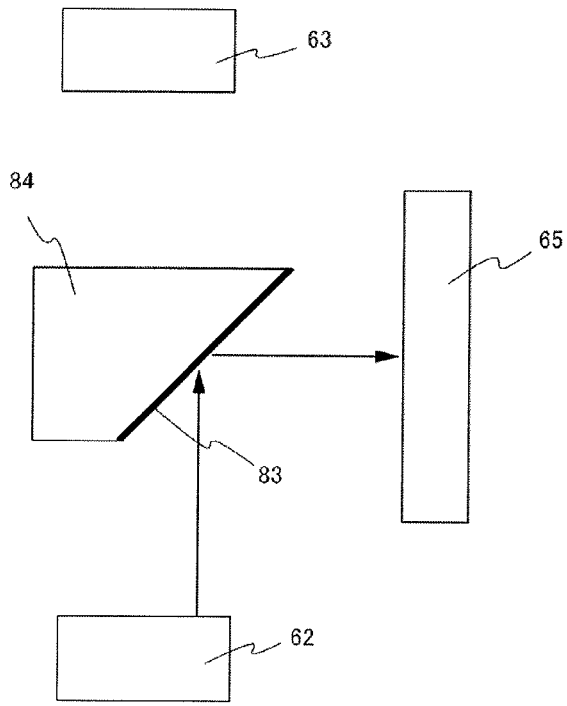

FIG. 18 illustrates an example where used are a pair of side-surface reference plate 84 of FIG. 16 in left and right reversed and upside down state.

In FIG. 18(*a*) the light emitted from the upper surface side light source 63 is reflected sideways by the upwardly facing reflection surface 83 of the side-surface reference plate 84, and in FIG. 18(*b*) the light emitted from the lower surface side light source 62 is reflected sideways by the downwardly facing reflection surface of the side-surface reference plate 84.

It should be noted that, when the pair of side-surface reference plates 84 are to be used, three reference plates will be mounted on the holding member 82 illustrated in FIG. 12.

According to the above-described respective side-surface reference plates 84, the side surface side photosensor 65 is capable of receiving substantially the same level of light as that reflected and/or transmitted from the side surface of the grain G with regard to the reflected and/or transmitted light received from the side surface of each side-surface reference plates 84.

Accordingly, in accordance with the grain quality level discrimination device 1 of the embodiment 3, it's possible to correct accurately the amount of the reflected and/or transmitted light from the upper and lower surfaces of the grain G as well as those from the side surface of the grain G.

The respective reflection surface 83 of each side-surface reference plates 84 is formed as a roughened surface through mechanical treatment such as blasting or chemical treatment such as etching, or any other treatment or process.

Accordingly, since the reflection surface 83 of the side-surface reference plate 84 is configured as a light diffusion surface provided by the roughened surface, the light reflected sideways on the reflection surface diffuses, so that the side surface side photosensor 65 can evenly receive the red, green, and blue lights from the side surface of the side-surface reference plate 84.

Further, the side-surface reference plate 84 can be adapted to have a color tone, for example, milky white, which diffuses the light reflected sideways on the reflection surface 83 and transmitted through the side-surface reference plate 84.

When the side-surface reference plate 84 has a color tone such as milky white or the like diffusing the transmitted light, the light reflected sideways on the reflection surface 83 and transmitted through the side-surface reference plate 84 diffuses so that the side surface side photosensor 65 can evenly receive the red, green, and blue lights from the side surface of the side-surface reference plate 84.

It should be noted that, when the side-surface reference plate 84 has the color tone causing the diffusion, it is not always necessary to configure the reflection surface as the roughened surface.

Also, although the reference plates 81, 84 are adapted to be mounted ordinally on the grain quality level discrimination device in the above-described embodiments of the present invention, the reference plates may be mounted temporarily on the device when the amount of light received by the photosensor is to be corrected.

The embodiments have been described in the foregoing.

However, the present invention is not limited to the embodiments and its features can be modified as appropriate without departing from the scope of the invention.

INDUSTRIAL APPLICABILITY

The grain quality level discrimination device of the present invention, which achieves highly accurate quality level discrimination, is very useful in determining quality level of grains G.

REFERENCE SIGNS LIST

1: Grain quality level discrimination device
2: Conveying unit
21: Disk
22: Recess
23: Bottom plate
24: Rotation shaft
3: Optical unit
31-35: Light source
41: Upper surface side photosensor
42: Side surface side photosensor
47: Collector lens
51: Dichroic short-pass filter
61: Reflection member
62: Lower surface side light source
63: Upper surface side light source
65: Side surface side photosensor
7: Quality level discrimination unit
81: Upper/lower-surface reference plate
82: Holding member
83: Reflection surface
84: Side-surface reference plate
91: Shaft
92: Rotating member
93: Gear
95: Motor
96: Gear
A: Grain measurement position
B: Reference plate position
G: Grain

The invention claimed is:

1. A grain quality level discrimination device comprising:
an optical unit having a plurality of light sources adapted to emit light to a grain and a photosensor adapted to receive reflected and/or transmitted light from the grain; and
a quality level discrimination unit configured to discriminate quality level of the grain on the basis of the light received by the photosensor,
the optical unit being configured such that
a particular light source configured to emit particular light from one surface side of the grain is included in the light sources, the particular light having a predetermined wavelength necessary for identifying a planar shape of the grain,
the photosensor includes a first light receiving area configured to receive reflected and/or transmitted light from the other surface side of the grain and a second light receiving area configured to receive reflected and/or transmitted light from the one surface side of the grain, and
an optical filter is provided on the one surface side of the grain, the optical filter arranged on a path of the particular light from the particular light source to the grain and being configured to transmit or reflect the particular light emitted by the particular light source;
the particular light source is configured to emit the particular light from the one surface side of the grain through the optical filter;
the first light receiving area is configured to receive the reflected and/or transmitted light from the other surface side of the grain including the transmitted light of the particular light from the particular light source, the particular light being emitted from the one surface side of the grain, and
the second light receiving area, which is arranged on the one surface side of the grain, is configured to receive the reflected and/or transmitted light from the one surface side of the grain through the optical filter.

2. The grain quality level discrimination device as set forth in claim 1, wherein the particular light is blue light in a blue wavelength range, and the particular light source is a blue light source.

3. The grain quality level discrimination device as set forth in claim 2, wherein the optical filter is a dichroic short-pass filter through which the blue light is transmitted, the blue light source is configured to emit the blue light transmitted through the dichroic short-pass filter from the one surface side of the grain, the first light receiving area is configured to receive the reflected and/or transmitted light from the other surface side of the grain including the transmitted blue light from the blue light source emitted from the one surface side of the grain and transmitted through the dichroic short-pass filter, and the second light receiving area is configured to receive the reflected and/or transmitted light from the one surface side of the grain, the reflected and/or transmitted light being reflected from the dichroic short-pass filter.

4. The grain quality level discrimination device as set forth in claim 2, wherein the dichroic filter is a dichroic long-pass filter configured to reflect blue light,
the blue light source is configured to emit blue light from the one surface side of the grain, the blue light being reflected from the dichroic long-pass filter,
the first light receiving area is configured to receive the reflected and/or transmitted light from the other surface side of the grain including the transmitted blue light from the blue light source emitted from the one surface side of the grain and reflected from the dichroic long-pass filter, and
the second light receiving area is configured to receive the reflected and/or transmitted light from the one surface side of the grain transmitted through the dichroic long-pass filter.

5. The grain quality level discrimination device as set forth in claim 1, wherein the photosensor includes a third light receiving area configured to receive reflected and/or transmitted light from a side surface of the grain.

6. The grain quality level discrimination device as set forth in claim 1, further comprising a conveying unit having a rotating disk that conveys the grain, wherein the optical unit is configured to emit light to the grain conveyed by the conveying unit and receives the reflected and/or transmitted light from the grain.

* * * * *